US011338104B2

(12) United States Patent
Klasek et al.

(10) Patent No.: US 11,338,104 B2
(45) Date of Patent: *May 24, 2022

(54) HUMIDIFIER FOR RESPIRATORY APPARATUS

(71) Applicant: ResMed Pty Ltd, Bella Vista (AU)

(72) Inventors: Paul Jan Klasek, Sydney (AU);
Alexander Virr, Gosford (AU);
Nathan John Row, Sydney (AU);
Ronald James Huby, Sydney (AU);
Jack Wei Cheng, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/494,503

(22) Filed: Oct. 5, 2021

(65) Prior Publication Data

US 2022/0023578 A1 Jan. 27, 2022

Related U.S. Application Data

(63) Continuation of application No. 15/710,893, filed on Sep. 21, 2017, which is a continuation of application
(Continued)

(30) Foreign Application Priority Data

Nov. 8, 2006 (AU) ................................ 2006906224

(51) Int. Cl.
*A61M 16/10* (2006.01)
*A61M 16/06* (2006.01)
(Continued)

(52) U.S. Cl.
CPC .... *A61M 16/1075* (2013.01); *A61M 16/0633* (2014.02); *A61M 16/0875* (2013.01);
(Continued)

(58) Field of Classification Search
CPC .......... A61M 16/1075; A61M 16/0633; A61M 16/108; A61M 16/1085; A61M 16/109; A61M 16/1095; A61M 16/16
See application file for complete search history.

(56) References Cited

U.S. PATENT DOCUMENTS 2,617,010 A 11/1952 Schmitz
3,871,373 A 3/1975 Jackson
(Continued)

FOREIGN PATENT DOCUMENTS

AU 14863/95 9/1995
CN 1204266 A 1/1999
(Continued)

OTHER PUBLICATIONS

Office Action dated Apr. 20, 2021 issued in Chinese Application No. 201910397235.1 with English translation (18 pages).
(Continued)

*Primary Examiner* — LaToya M Louis
(74) *Attorney, Agent, or Firm* — Nixon & Vanderhye P.C.

(57) ABSTRACT

A heated conduit is configured to be connected to and receive pressurized breathable gas from a respiratory unit. The heated conduit includes a first cuff configured to be attached to the respiratory unit, the first cuff comprising a tubular air inlet portion that is configured to receive the pressurized breathable gas and an electrical connector portion that is adjacent to the tubular air inlet portion and comprises three electrical terminals. The three electrical terminals are configured to engage an electrical connector of the respiratory unit. A grouping of wires are supported within a helical rib of a flexible tube portion. The grouping of wires includes a pair of heating wires configured to generate heat and a signal wire configured to carry the signal that is output by a sensing device. Each of the heating wires and the signal wire is connected to a corresponding one of
(Continued)

the three electrical terminals of the electrical connector portion of the first cuff.

27 Claims, 30 Drawing Sheets

Related U.S. Application Data

No. 11/936,822, filed on Nov. 8, 2007, now Pat. No. 9,855,398.

(60) Provisional application No. 60/955,222, filed on Aug. 10, 2007.

(51) Int. Cl.
  *A61M 16/08* (2006.01)
  *A61M 16/16* (2006.01)
  *A61M 16/00* (2006.01)

(52) U.S. Cl.
  CPC ........ *A61M 16/108* (2014.02); *A61M 16/109* (2014.02); *A61M 16/1085* (2014.02); *A61M 16/1095* (2014.02); *A61M 16/16* (2013.01); *A61M 16/0066* (2013.01); *A61M 16/06* (2013.01); *A61M 16/0816* (2013.01); *A61M 16/161* (2014.02); *A61M 2016/0027* (2013.01); *A61M 2016/0039* (2013.01); *A61M 2205/14* (2013.01); *A61M 2205/3368* (2013.01); *A61M 2205/3375* (2013.01); *A61M 2205/3569* (2013.01); *A61M 2205/3584* (2013.01); *A61M 2205/3592* (2013.01); *A61M 2205/3633* (2013.01); *A61M 2205/3653* (2013.01); *A61M 2205/6018* (2013.01); *A61M 2205/6054* (2013.01); *A61M 2230/04* (2013.01)

(56) References Cited

U.S. PATENT DOCUMENTS

| | | | |
|---|---|---|---|
| 4,038,519 A | 7/1977 | Foucras |
| 4,060,576 A | 11/1977 | Grant |
| 4,516,573 A | 5/1985 | Gedeon |
| 4,621,632 A | 11/1986 | Bartels et al. |
| 4,686,354 A | 8/1987 | Makin |
| 4,708,831 A | 11/1987 | Elsworth et al. |
| 4,967,744 A | 11/1990 | Chua |
| 5,031,612 A | 7/1991 | Clementi |
| 5,163,423 A | 11/1992 | Suzuki |
| 5,230,331 A | 7/1993 | Rusz et al. |
| 5,357,948 A | 10/1994 | Eilentropp |
| 5,392,770 A | 2/1995 | Clawson et al. |
| 5,454,061 A | 9/1995 | Carlson |
| 5,468,961 A | 11/1995 | Gradon et al. |
| 5,512,732 A | 4/1996 | Yagnik |
| 5,537,996 A | 7/1996 | McPhee |
| 5,558,084 A | 9/1996 | Daniell et al. |
| 5,640,951 A | 6/1997 | Huddart et al. |
| 5,988,164 A | 11/1999 | Paluch |
| 6,010,118 A | 1/2000 | Milewicz |
| 6,050,260 A | 4/2000 | Daniell |
| 6,078,730 A | 6/2000 | Huddart et al. |
| 6,167,883 B1 | 1/2001 | Beran et al. |
| 6,367,472 B1 | 4/2002 | Koch |
| 6,437,316 B1 | 8/2002 | Colman et al. |
| 6,584,972 B2 | 7/2003 | McPhee |
| 6,598,604 B1 | 7/2003 | Seakins |
| 6,918,389 B2 | 7/2005 | Seakins |
| 6,953,354 B2 | 10/2005 | Edirisuriya et al. |
| 7,086,399 B2 | 8/2006 | Makinson et al. |
| 7,140,367 B2 | 11/2006 | White et al. |
| 7,306,205 B2 | 12/2007 | Huddart et al. |
| 9,750,917 B2 | 9/2017 | Seakins et al. |
| 9,855,398 B2 | 1/2018 | Klasek et al. |
| 2002/0112725 A1 | 8/2002 | Thudor et al. |
| 2002/0124847 A1 | 9/2002 | Smith et al. |
| 2003/0132535 A1 | 7/2003 | Lipscombe |
| 2003/0154977 A1 | 8/2003 | White et al. |
| 2004/0079370 A1 | 4/2004 | Gradon et al. |
| 2004/0081784 A1 | 4/2004 | Smith et al. |
| 2004/0102731 A1 | 5/2004 | Blackhurst et al. |
| 2004/0149284 A1 | 8/2004 | Smith et al. |
| 2004/0182392 A1 | 9/2004 | Gerder et al. |
| 2004/0221844 A1 | 11/2004 | Hunt et al. |
| 2006/0137445 A1 | 6/2006 | Smith et al. |
| 2006/0278221 A1 | 12/2006 | Schermeier et al. |
| 2007/0283957 A1 | 12/2007 | Schobel (nee Bauer) et al. |
| 2008/0028850 A1 | 2/2008 | Payton et al. |
| 2008/0105257 A1 | 5/2008 | Klasek et al. |
| 2009/0078440 A1 | 3/2009 | Carlson et al. |
| 2018/0028773 A1 | 2/2018 | Klasek et al. |

FOREIGN PATENT DOCUMENTS

| | | |
|---|---|---|
| CN | 1314192 A | 9/2001 |
| CN | 1341463 A | 3/2002 |
| CN | 1370085 A | 9/2002 |
| CN | 1267167 C | 8/2006 |
| CN | 101018582 A | 8/2007 |
| DE | 40 34 611 A1 | 5/1992 |
| DE | 200 18 593 U1 | 2/2001 |
| DE | 202 02 906 U1 | 6/2002 |
| EP | 0 097 901 A2 | 1/1984 |
| EP | 0 201 985 A1 | 11/1986 |
| EP | 0 258 928 A1 | 3/1988 |
| EP | 1 295 621 A2 | 3/2003 |
| GB | 897 292 A | 5/1962 |
| GB | 2 116 434 A | 9/1983 |
| GB | 2 173 274 A | 10/1986 |
| GB | 2252739 | 8/1992 |
| GB | 2 277 689 A | 11/1994 |
| JP | 58-192555 A | 11/1983 |
| JP | 61-232864 A | 10/1986 |
| JP | 4-25753 U | 2/1992 |
| JP | 4-38962 A | 2/1992 |
| JP | 5-113237 | 5/1993 |
| JP | 5-317428 A | 12/1993 |
| JP | 9-234247 | 9/1997 |
| JP | 2876373 | 3/1999 |
| JP | 2000-500359 A | 1/2000 |
| JP | 2000-512518 A | 9/2000 |
| JP | 2001-314508 A | 11/2001 |
| JP | 2003-245353 A | 9/2003 |
| JP | 2004-148817 A | 5/2004 |
| JP | 2006-271953 A | 10/2006 |
| SU | 379270 | 4/1973 |
| WO | 97/47348 A1 | 12/1997 |
| WO | 00/21602 A1 | 4/2000 |
| WO | 01/13981 A1 | 3/2001 |
| WO | 02/32486 A1 | 4/2002 |
| WO | 03/055554 A1 | 7/2003 |
| WO | 2004/011072 A1 | 2/2004 |
| WO | 2004/112873 A1 | 12/2004 |
| WO | 2004/1058484 A1 | 12/2004 |
| WO | 2005/021076 A2 | 3/2005 |
| WO | 2005/079898 A2 | 9/2005 |
| WO | 2006/019323 A1 | 2/2006 |

OTHER PUBLICATIONS

Extended European Search Report dated Jan. 21, 2021 issued in European Application No. 20185762.0 (8 pages).
Sep. 3, 2018 Further Examination Report issued in New Zealand Application No. 730968 (1 page).
Oct. 30, 2018 Further Examination Report issued in New Zealand Application No. 730968 (2 pages).
Fourth Office Action dated Mar. 1, 2018 issued in Chinese Application No. 201410069663.9 with English translation (12 pages).
Office Action dated Aug. 16, 2017 issued in Chinese Application No. 201410069663.9 with English translation (13 pages).
First Examination Report dated May 29, 2014 in Australian Application No. 2013257505 (3 pages).

(56) References Cited

OTHER PUBLICATIONS

Decision of Rejection dated Sep. 8, 2014 issued in Japanese Application No. 2012-188354 with English translation (5 pages).
Notice of Reasons for Rejection dated Aug. 29, 2016 issued in Japanese Application No. 2015-002424 with English translation (10 pages).
Further Examination Report dated Jun. 2, 2015 issued in New Zealand Application No. 625605 (1 page).
Notice of Reasons for Rejection dated Dec. 14, 2015 issued in Japanese Application No. 2015-002424 with English translation (8 pages).
Further Examination Report dated Dec. 11, 2015 issued in New Zealand Application No. 625605 (2 pages).
Decision of Rejection dated Oct. 31, 2016 issued in Chinese Application No. 201410069663.9 with English translation (18 pages).
Notice of Reasons for Rejection dated Aug. 20, 2013 in Japanese Application No. 2012-188354 with English translation (10 pages).
Supplementary European Search Report dated Sep. 3, 2013 in European Application No. 07815519.9 (3 pages).
Notification of the First Office Action dated Sep. 6, 2015 issued in Chinese Application No. 201410069663.9 with English translation (23 pages).
Notification of Second Office Action dated Apr. 25, 2016 issued in Chinese Application No. 201410069663.9.
Notice of Reasons of Rejection dated Apr. 28, 2014 in Japanese Application No. 2012-188354, with English translation (7 pages).
European Communication dated Sep. 13, 2013 in European Application No. 07 815 519.9 (5 pages).
Notification of the Fourth Office Action dated Sep. 4, 2013 in Chinese Application No. 200780044030.0, with English translation (11 pages).
The Free Online Dictionary, "definition of contact", Sep. 19, 2013, http//www.thefreedictionary.com/contact, pp. 1-3.
Z. Suo, "Temperature", Feb. 24, 2007, Statistical Thermodynamics, http://iMechanica.org/node/291, pp. 1-11.
Morris, Gary P. et al, "Thermal Contact", Dec. 22, 2008, MDPI, Entropy 2008, 10, 786-798; DOI: 10.3390/e10040786, www.mdpi.com/journal/entropy.
Notification of the Third Office Action dated May 21, 2013 in Chinese Application No. 200780044030.0, with English translation (12 pages).
Further Examination Report dated Jan. 25, 2013 in New Zealand Application No. 597827 (2 pages).
First Examination Report dated Jan. 23, 2013 in New Zealand Application No. 605326 (2 pages).
Notice of Reasons for Rejection dated Mar. 12, 2013 in Japanese Application No. 2009-534963, with English translation (8 pages).
Notification of Second Office Action dated Nov. 2, 2012 in Chinese Application No. 200780044030.0, with English translation (9 pages).
Australian Patent Examination Report No. 1 dated Nov. 29, 2012 in Australian Application No. 2007317198 (5 pages).
Notice of Reasons for Rejection dated May 29, 2012 in Japanese Application No. 2009-534963 with English translation (10 pages).
New Zealand Examination Report dated Jan. 31, 2012 in New Zealand Appln. No. 575837 (2 pages).
New Zealand Examination Report dated Jan. 31, 2012 in New Zealand Appln. No. 597827 (2 pages).
Fairchild Semiconductor, "MM74HC74A Dual D-Type Flip-Flop with Preset and Clear," Sep. 1983 (Revised Jan. 2005), pp. 1-8.
TelCom Semiconductor, Inc., "3-Pin µP Reset Monitors," TCM809/810-04, Aug. 29, 1996, pp. 5-15 through 5-18.
Unitrode Products from Texas Instruments, "Current Mode PWM Controller," SLUS224A, Sep. 1994 (Revised Apr. 2002), 11 pages.
National Semiconductor Corporation, "LP339 Ultra-Low Power Quad Comparator," DS005226, Aug. 2000, pp. 1-12.
Examination Report dated Dec. 23, 2010 in New Zealand Application No. 575837 (2 pages).
Notice of Grant dated Nov. 31, 2021 issued in Chinese Application No. 201910397235.1 with English translation (7 pages).

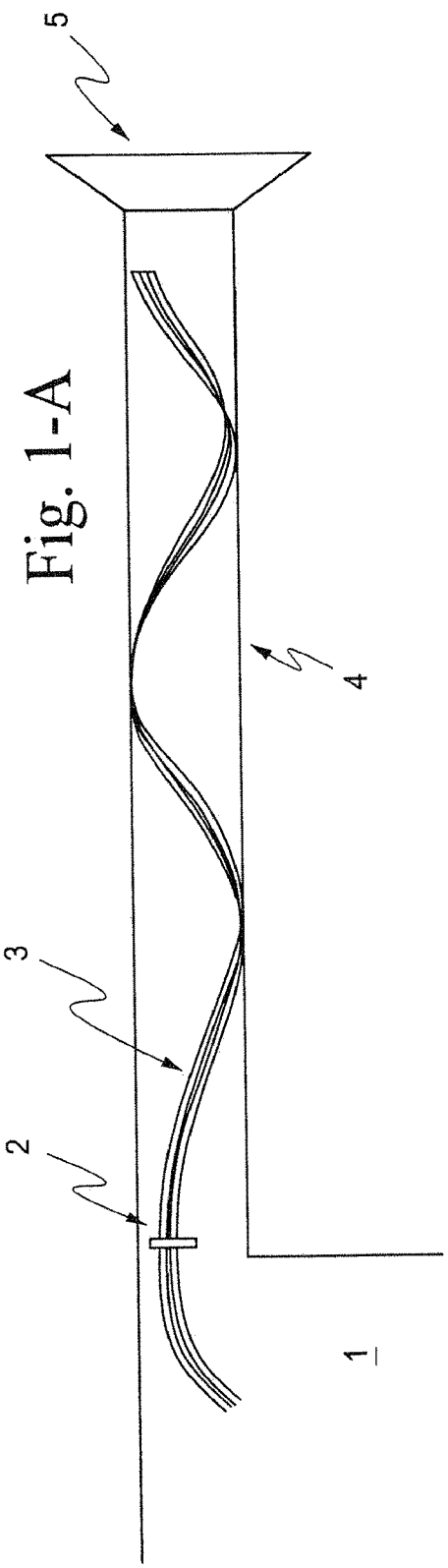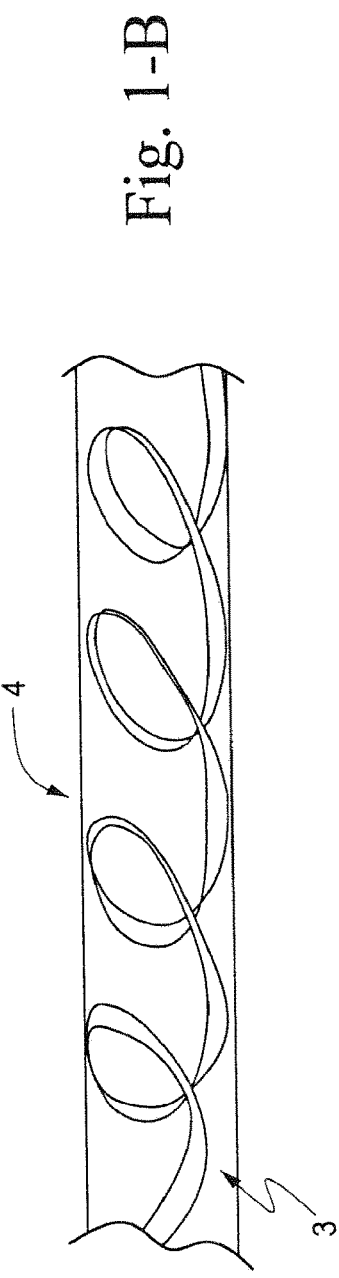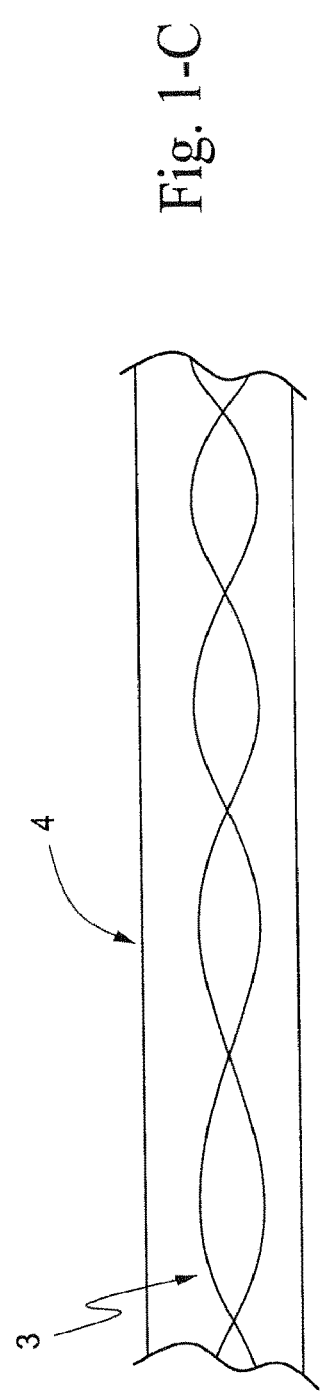

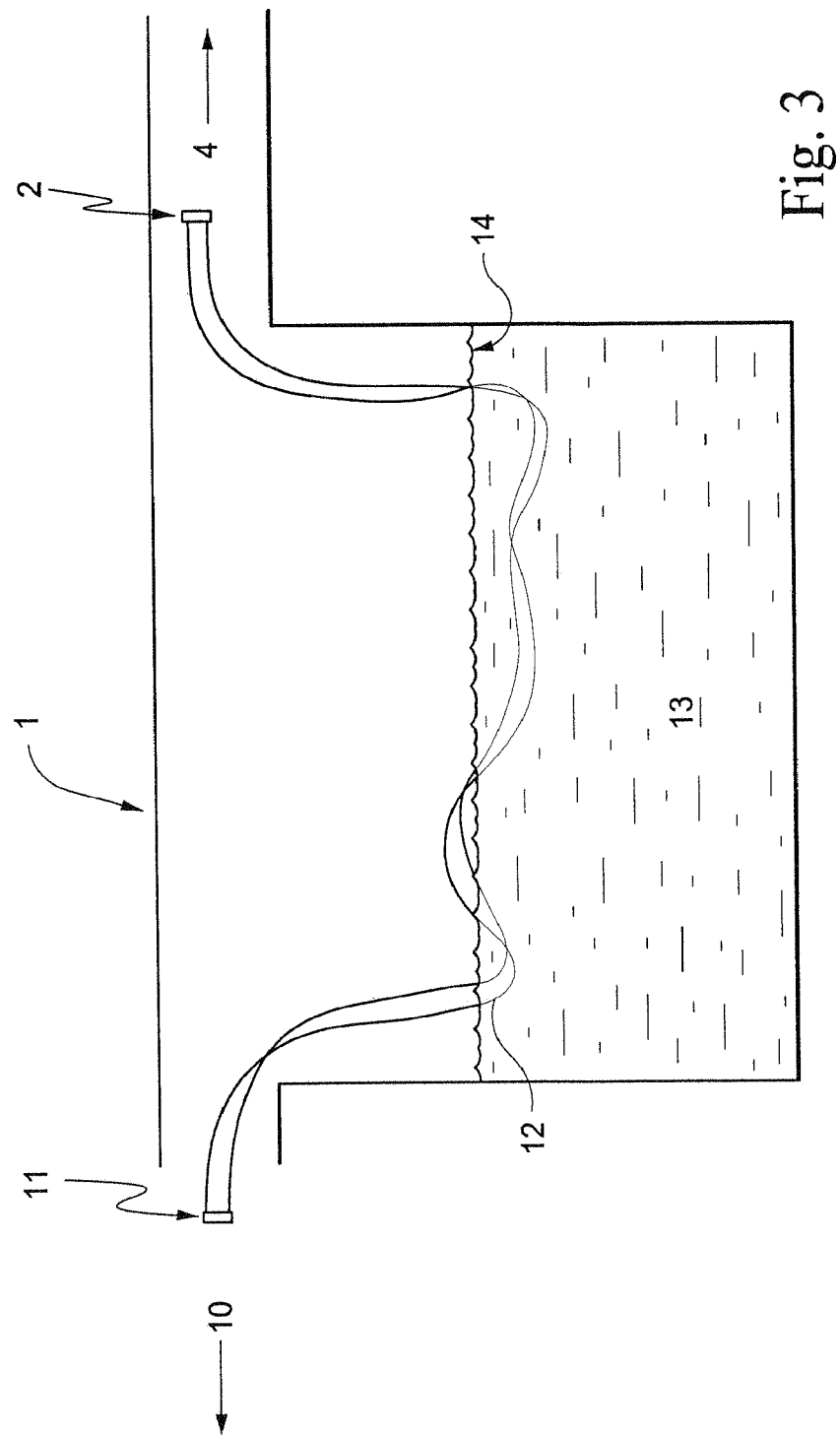

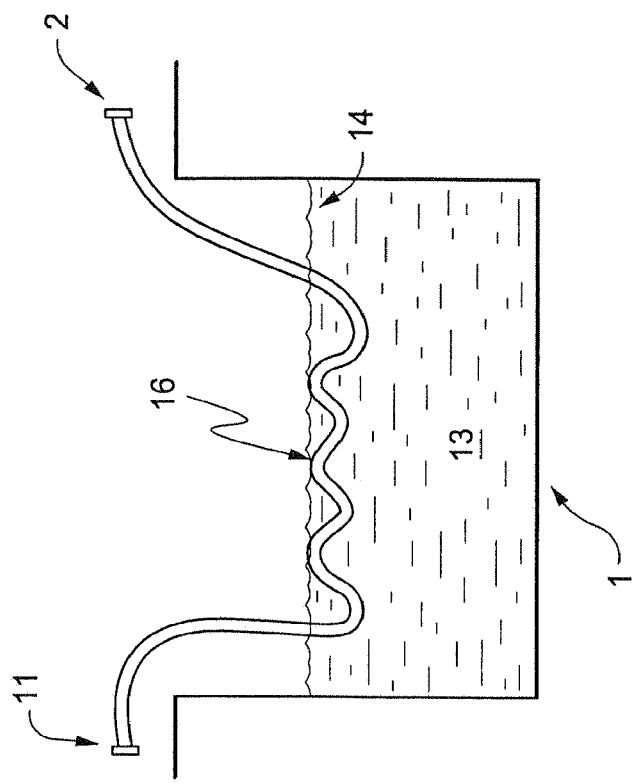
Fig. 4-A
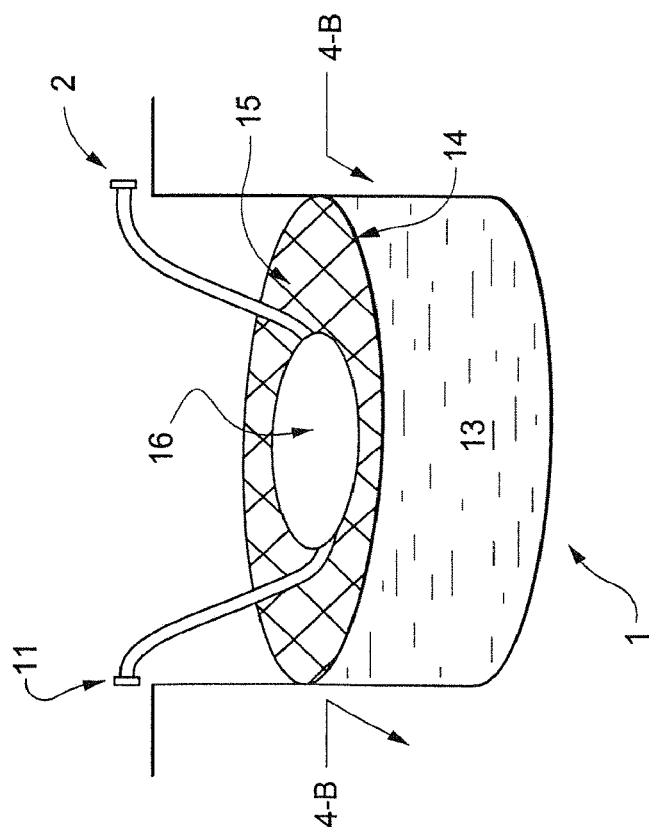
Fig. 4-B

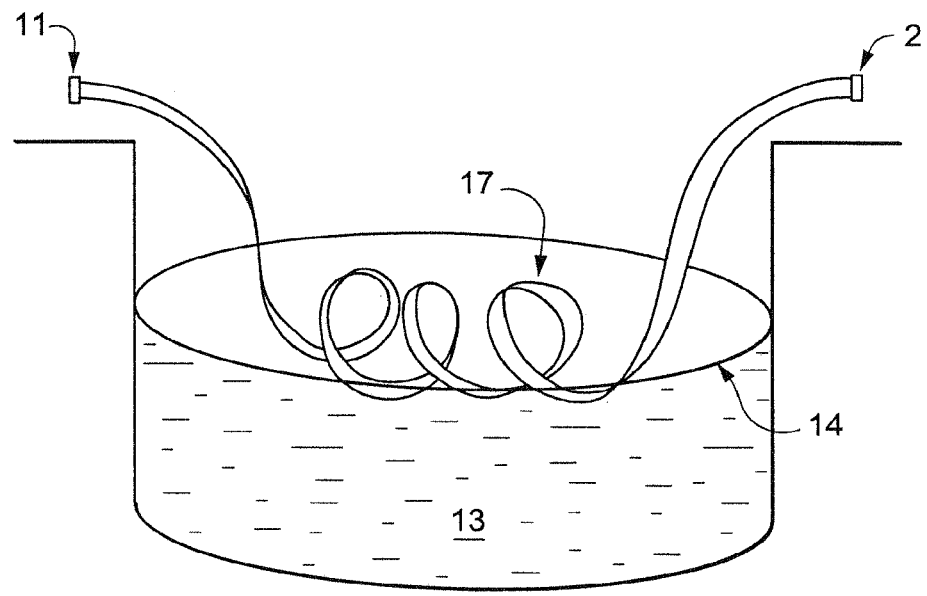
Fig. 4-C
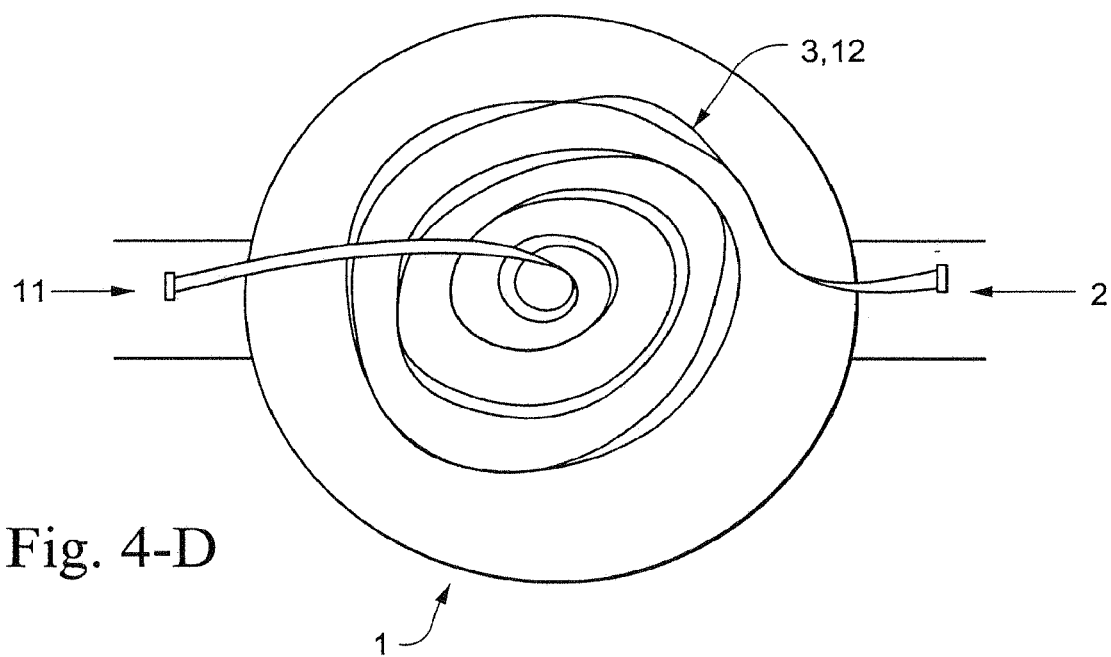
Fig. 4-D

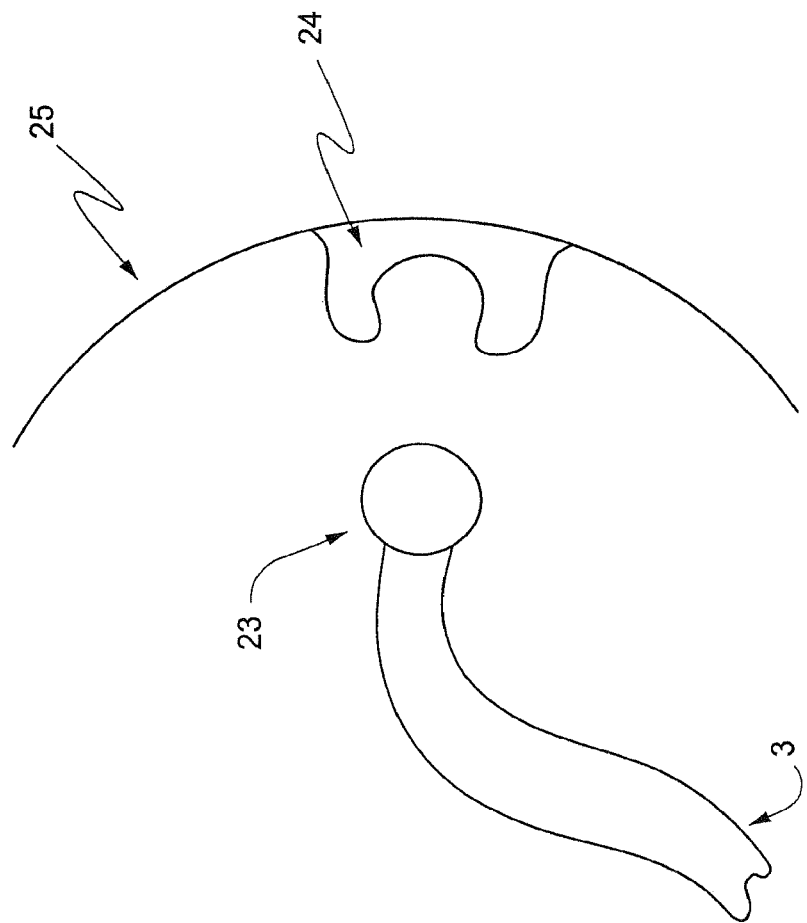
Fig. 6-B
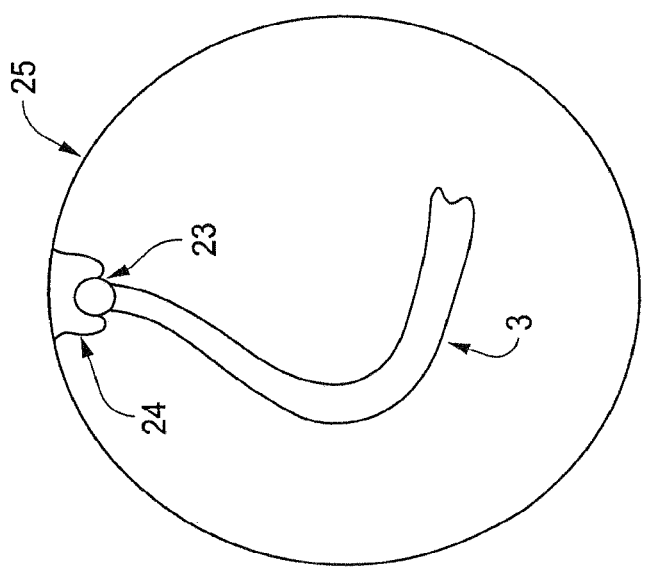
Fig. 6-A

HUMIDIFIER FOR RESPIRATORY APPARATUS

CROSS REFERENCE TO RELATED APPLICATIONS

This application is a continuation of U.S. application Ser. No. 15/710,893, filed Sep. 21, 2017, which is a continuation of U.S. application Ser. No. 11/936,822, now U.S. Pat. No. 9,855,398, which claims priority to U.S. Application 60/955,222, filed Aug. 10, 2007, and to Australian Provisional Application 2006906224, filed Nov. 8, 2006, the entire contents of each of which are incorporated herein by reference.

BACKGROUND OF THE INVENTION

1. Field of the Invention

The present invention relates to humidification and heater arrangements used to control the humidity of breathable gases used in all forms of respiratory apparatus ventilation systems including invasive and non-invasive ventilation, Continuous Positive Airway Pressure (CPAP), Bi-Level therapy and treatment for sleep disordered breathing (SDB) conditions such as Obstructive Sleep Apnea (OSA), and for various other respiratory disorders and diseases.

2 Description of Related Art

Respiratory apparatus commonly have the ability to alter the humidity of the breathable gas in order to reduce drying of the patient's airway and consequent patient discomfort and associated complications. The use of a humidifier placed between the flow generator and the patient mask, produces humidified gas that minimizes drying of the nasal mucosa and increases patient airway comfort. In addition in cooler climates, warm air applied generally to the face area in and about the mask, as may occur inadvertently by a leak, is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified pressurized gas to the patient's mask.

Typically, the heating element is incorporated in a heater plate which sits under, and is in thermal contact with, the water tub.

The humidified air may cool on its path along the conduit from the humidifier to the patient, leading to the phenomenon of "rain-out", or condensation, forming on the inside of the conduit. To counter this, it is known to additionally heat the gas being supplied to the patient by means of a heated wire circuit inserted into the patient conduit which supplies the humidified gas from the humidifier to the patient's mask. Such a system is illustrated in Mosby's Respiratory Care Equipment (7$^{th}$ edition) at page 97.

Such a heating method for the patient conduit may only provide poor heat transfer due to the wire locating itself along the conduit wall rather than in the main gas stream. A wire will also only give poor turbulent mixing due to its low profile. As a result heat transfer may be poor and the mixing of water vapor and gas may also be poor.

Alternatively the heating wire circuit may be located in the wall of the patient conduit. Such a system is described in U.S. Pat. No. 6,918,389.

U.S. Pat. No. 6,918,389 describes a number of humidifier arrangements for supplying low relative humidity, high temperature humidified gas to the patient. Some of these arrangements include pre- or post-heating of the gas to reduce the relative humidity.

None of these prior art devices provides an entirely satisfactory solution to the provision of comfortable humidified breathable gas to the patient, nor to ease of construction and hygiene requirements and to energy and patient comfort requirements at startup.

SUMMARY OF THE INVENTION

Examples of the present invention aim to provide an alternative humidifier arrangement which overcomes or ameliorates the disadvantages of the prior art, or at least provides a useful choice.

In one sample embodiment of the invention, a humidifier and/or temperature or other sensing or control apparatus for use with respiratory apparatus comprises a heating filament in thermal contact with the gas and/or water, wherein the filament is in the form of an elongate tape. The tape may be flexible, and may, in a sample embodiment, be passed along the bore of the patient gas conduit, or incorporated into the conduit wall.

In another sample embodiment, a humidifier for use with respiratory apparatus comprises a heater in contact with water in the humidifier tub, and which floats or otherwise rises and falls with changes in the water level in the humidifier tub.

In a further form, the invention provides a humidifier arrangement for respiratory apparatus, including an elongate filament heater in contact with the air path in the regions before and after the humidification chamber. The filament heater may be further in contact with a body of water in the humidification chamber.

Heating of the filament may be divided into two or more separately controllable zones.

A further sample embodiment of the invention provides a method of increasing patient comfort during start-up of humidification, the method comprising providing a heating element to thermally contact breathable gas being provided to the patient along a gas flow path and to thermally contact water in a humidifier apparatus; and configuring the heating element to heat the gas in the gas flow path and to heat the water in the humidifier apparatus, such the patient is initially provided with heated gas while the temperature of the water in the humidifier apparatus is being increased to its operating temperature.

The heating of the gas in the gas flow path may include heating of a part of the gas flow path upstream of a humidification chamber such that passage of the heated gas through the humidifier apparatus provides an initial degree of humidification.

According to a sample embodiment of the invention, a conduit for use in a respiratory apparatus for delivering breathable gas to a patient comprises a tube; a helical rib on an outer surface of the tube; and a plurality of wires supported by the helical rib in contact with the outer surface of the tube.

According to another sample embodiment of the invention, the conduit may further comprise a connector block connected to an end of the conduit, wherein the connector block is configured to be connected to a flow generator or a patient interface of the respiratory apparatus.

According to a further sample embodiment of the invention, a respiratory apparatus for delivering breathable gas to a patient, comprises a flow generator to generate a supply of pressurised gas to be delivered to the patient; a humidifier to vaporize water and to deliver water vapor to humidify the gas; a first gas flow path leading from the flow generator to the humidifier; and a second gas flow path leading from the humidifier to a patient interface, wherein the first gas flow path comprises a first conduit having a first connector block configured to be connected to the flow generator and the second gas flow path comprises a second conduit having a second connector block configured to be connected to the patient interface.

According to still another sample embodiment of the invention, a method of delivering breathable gas to a patient comprises delivering a humidified flow of breathable gas to a patient interface via a conduit; heating the conduit by supplying a DC current at a predetermined duty cycle to a plurality of wires supported by the conduit; sensing a temperature in the conduit during an OFF cycle of the predetermined duty cycle; and controlling the DC current to maintain the temperature in the conduit at a selected temperature.

BRIEF DESCRIPTION OF THE DRAWINGS

Embodiments of the invention will now be described with reference to the accompanying drawings, in which:

FIG. 1-A is a schematic side sectional view of the patient conduit with a flexible tape heater in an embodiment of the present invention;

FIG. 1-B is an alternative embodiment of FIG. 1-A where the flexible tape heater is in a helical configuration;

FIG. 1-C: is an alternative embodiment of FIG. 1-A where the flexible tape heater is twisted about its longitudinal axis;

FIG. 3 is a schematic side sectional view of the humidification chamber with an embodiment of the floating heater;

FIG. 4-A is a side perspective view of an embodiment of the floating heater, a circular floating plate heater which is secured under a floating plastic support grid;

FIG. 4-B is a side perspective view of another embodiment of a floating heater;

FIG. 4-C is a perspective side view of another embodiment of a floating, helical flexible tape heater;

FIG. 4-D is a plan view of another embodiment of a flexible tape heater wound in a horizontal spiral;

FIG. 6-A is a transverse cross-sectional view of the patient conduit showing the flexible tape heater connected to the conduit wall;

FIG. 6-B is another view of the connector embodiment of FIG. 6-A where the connector is disengaged;

FIGS. 37b-1 to 37b-4 schematically illustrate a sample embodiment of the circuit of FIG. 37a;

DETAILED DESCRIPTION

Flexible Tape Heater

Figure 37A:
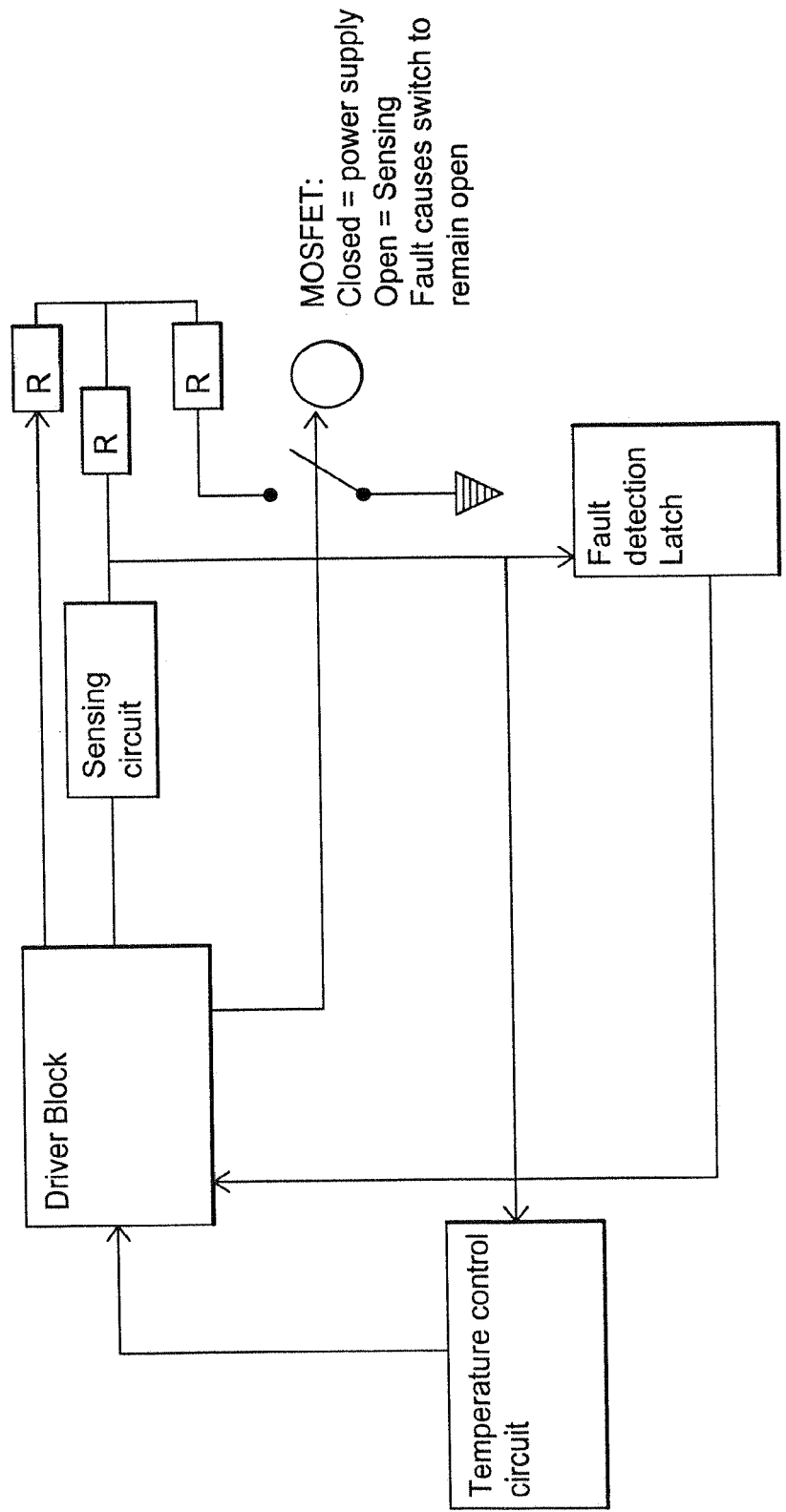
FIG. 37a schematically illustrates a sample embodiment of the circuits of the power supply/controller.
Figures 1, 37B:
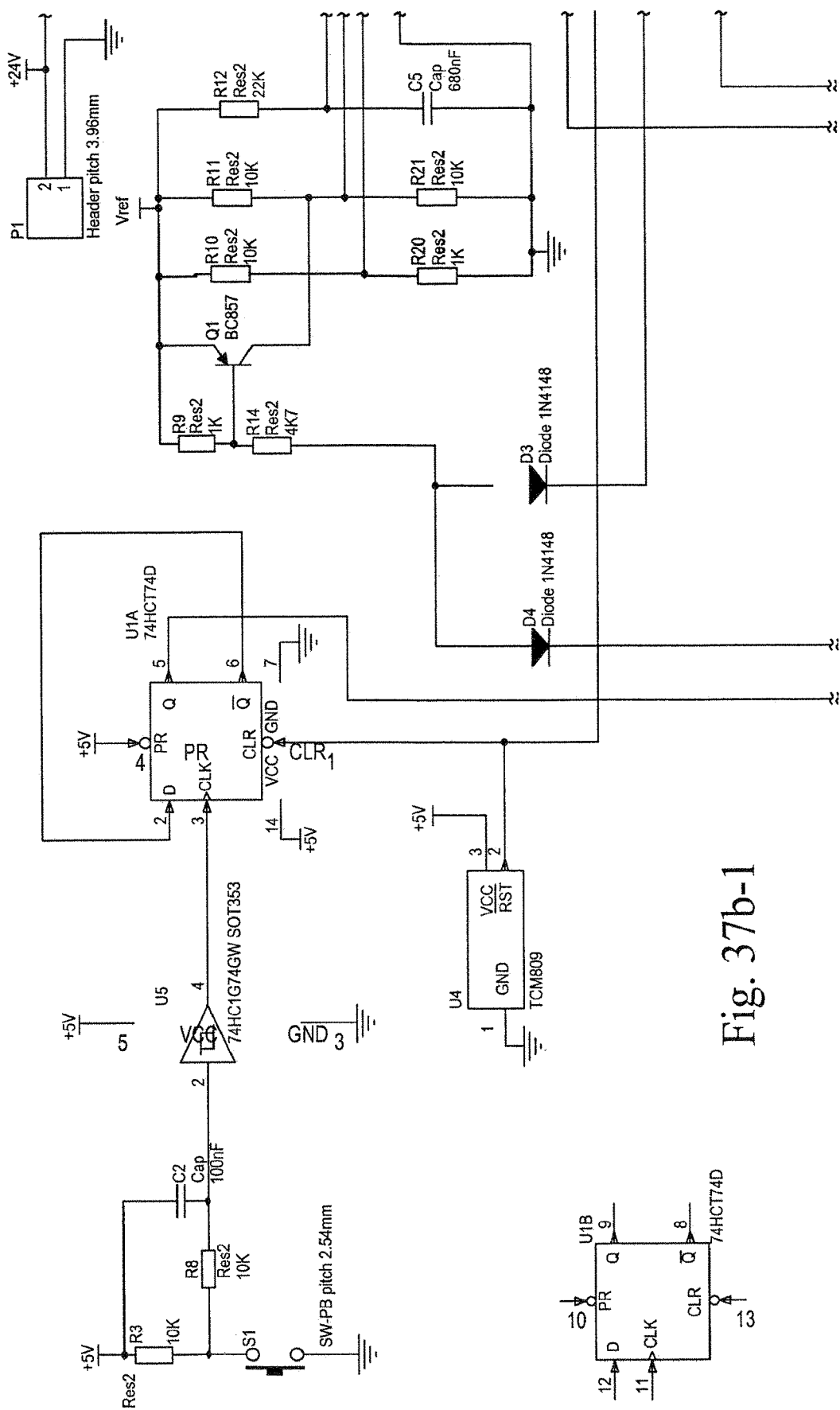
Figures 2, 37B:
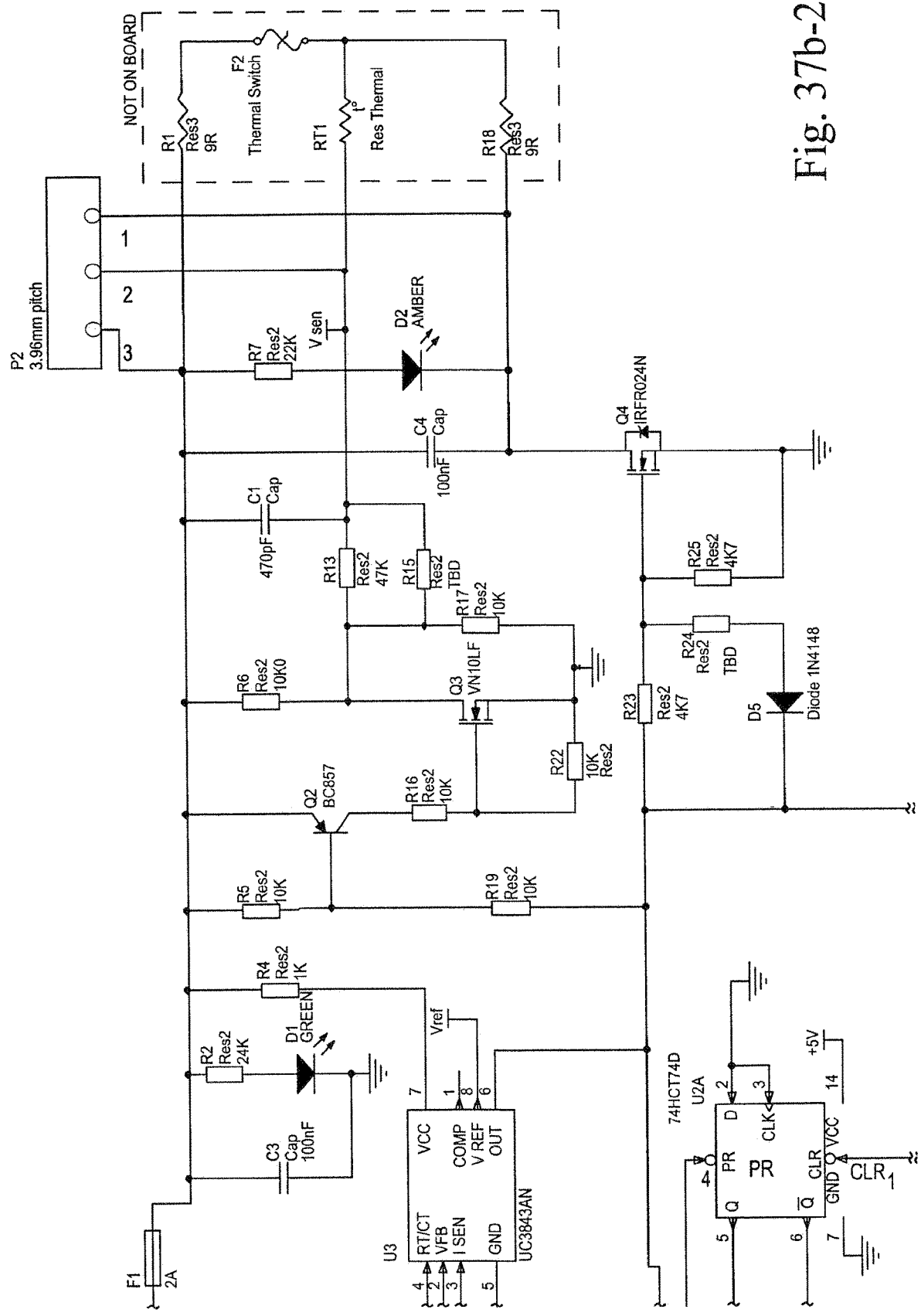

FIGS. 1-A to 1-C illustrate the use of a flexible tape heater 3 within the patient conduit 4 of a respiratory apparatus. The patient conduit 4 is located between the humidification chamber 1 and the patient interface, e.g. mask 5. The patient conduit 4 conveys the flow of gas from the humidification chamber 1 to the patient mask 5 in respiratory apparatus. The humidification chamber 1 in turn receives pressurized gas from a flow generator 20 (FIG. 5) or blower.

The flexible tape heater 3 in the patient conduit 4 is used to heat the flow of gas in the patient conduit 4. Heating of the gas enables the gas comfort features of temperature and humidity to be attained and maintained for the gas delivered by the respiratory apparatus.

The flexible tape heater 3 is electrically coupled to a heater controller 21 (FIG. 5) by a patient conduit connector end 2. The heater controller 21 may be incorporated in the humidifier or the flow generator 20 or the base unit 22, or be a separate unit 21, for example supplying a DC voltage of, for example, 0.1-24V.

The patient conduit connector end 2 may connect to the heater controller 21 via another flexible tape heater (partially shown on the left side in FIG. 1) or to the conduit wall 25, of the patient conduit 4, via a connector 23, 24 shown in FIGS. 6-A and 6-B. The connector may include a male connector element 23 and a female connector element 24 which may make an electrical, communications and/or mechanical connection between the flexible tape heater 3 and the conduit wall 25. The male connector element 23 and the female connector element 24 may be interchangeable in position. The connector 23, 24 locks the flexible tape heater 3 in position on the conduit wall 25, but may also be disengaged. The connector 23, 24 may be used at any location along or around the conduit wall 25.

The patient conduit 4 may be insulated or a heated conduit as in the prior art in order to reduce heat loss and minimize consequent water condensation or "rain-out" within the patient conduit 4. The insulation could be an outer sleeve or wrapping about the patient conduit 4. The outer sleeve or wrapping could be foam, fabric or an air space in the case of a double walled conduit.

In another embodiment the flexible tape heater 3 may be combined with the wall of the patient conduit 4 in order to provide heating to the wall to prevent condensation, while optionally an additional flexible tape heater 3 within the patient conduit 4 provides the heating to the gas flow.

In a further embodiment the patient conduit 4 is formed by making a helix of the flexible tape heater 3 and joining the edges the flexible tape heater 3 to form the patient conduit 4.

The flexible tape heater 3 should be sufficiently flexible so that in use flexing of the patient conduit 4 is not restricted. The flexibility of the flexible tape heater 3 also should be sufficient to enable insertion and removal of the flexible tape heater 3 within the patient conduit 4, while being sufficiently stiff so that the flexible tape heater 3 can be inserted into the patient conduit 4 and will support itself in a desired position and not collapse against a wall or to one end of the patient conduit 4. Additionally the stiffness should be sufficient so that the flexible tape heater 3 will not flutter in the gas stream to produce an unwanted audible noise.

The thin, flat and extended nature of the flexible tape heater 3 enhances heat transfer with the gas flow while also providing low impedance to the gas flow. The flexible tape heater 3 can be placed in the patient conduit 4 such that it has a helical configuration (FIG. 1-B) and/or the flexible tape heater 3 can be twisted or bent about one or more of the flexible tape heater 3 axes. The longitudinal axis twist configuration is illustrated in FIG. 1-C.

Alternative profiles or geometric structures for the flexible heating tape may include:

The transverse cross-section of the flexible tape heater may be rectangular, elliptical or arbitrary;

The surface of the flexible tape heater 3 may be rough or smooth or dimpled; and/or One or more surfaces of the flexible tape heater 3 may be rippled.

The dimensions of the thickness and width may vary along the length of the flexible tape heater. For example a thicker section of the flexible tape heater 3 in the patient conduit 4 may be provided to give a venturi effect of increasing the gas flow rate so that flow detection may be possible by pressure sensors along the length of the flexible tape heater 3.

The use of these twisted, helical or other configurations described above increases the length of the flexible tape heater 3 in the patient conduit 4 and thus the available surface area for heat transfer between the gas flow and the surface of the flexible tape heater 3. Additionally these configurations can be used to enhance the turbulent mixing of the water vapor produced in humidification chamber 1 with the gas flow.

Figure 5:
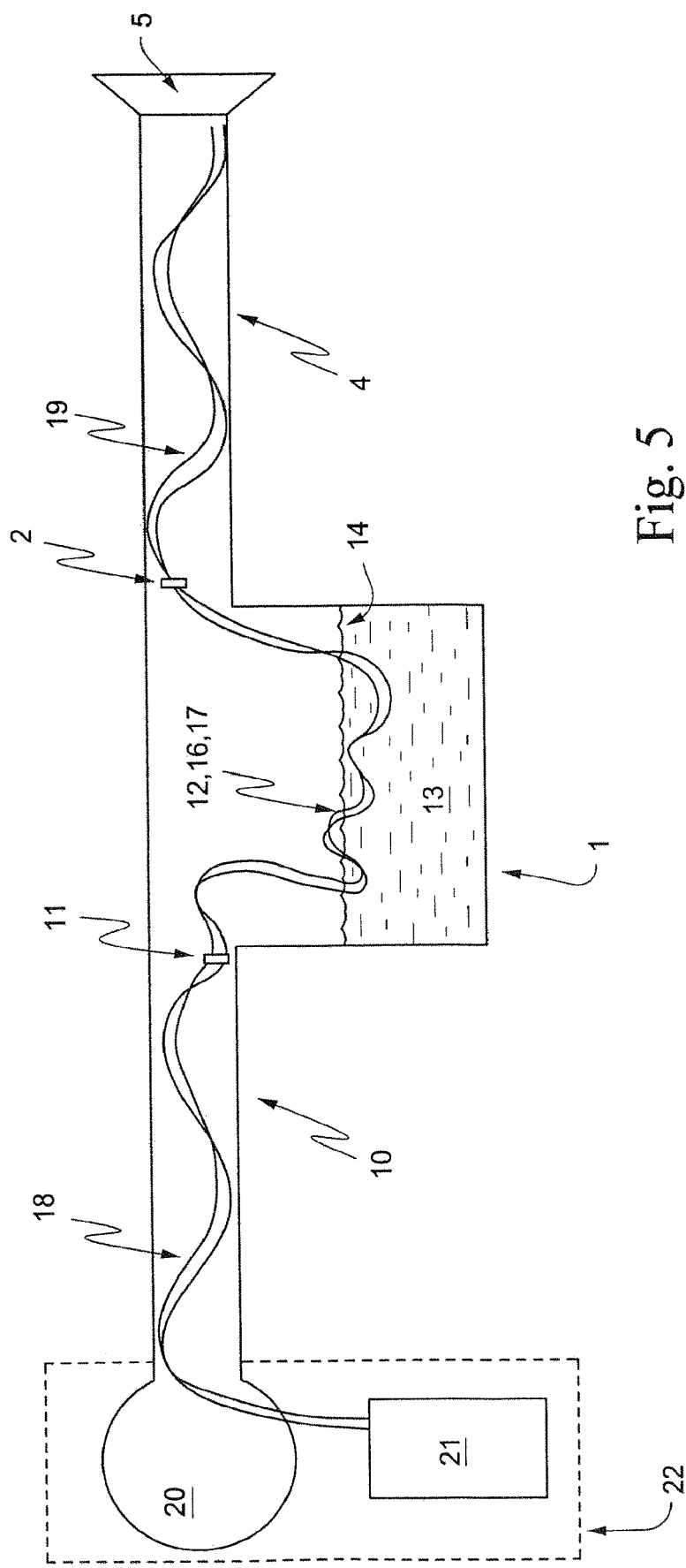
FIG. 5 schematically illustrates a humidification heater arrangement comprising multiple zones.

The various configurations may also be used to provide zones of differing flow, acoustic, humidity or temperature properties along the patient conduit 4 or the apparatus as a whole, as show in FIG. 5 for example.

It may be desirable to modify the acoustic impedance properties of the patient conduit 4 using the flexible tape heater 3. For example:

The generation or reduction in white noise (broad frequency spectrum noise);

The damping or filtering of a particular acoustic noise frequency component/s, e.g. structure-borne or air-borne flow generator tonal noise; and/or Enhancement of the propagation of patient respiratory acoustic signals through the patient conduit 4 and to the base unit 22 (FIG. 5) for monitoring and diagnosis.

The alteration of acoustic impedance properties using the flexible tape heater 3 may be achieved by the choice of the materials making up the flexible tape heater 3 and the configurations described above of the flexible tape heater 3 in the patient conduit 4, and additionally as shown in FIGS. 1-A to 1-C.

Figure 2:
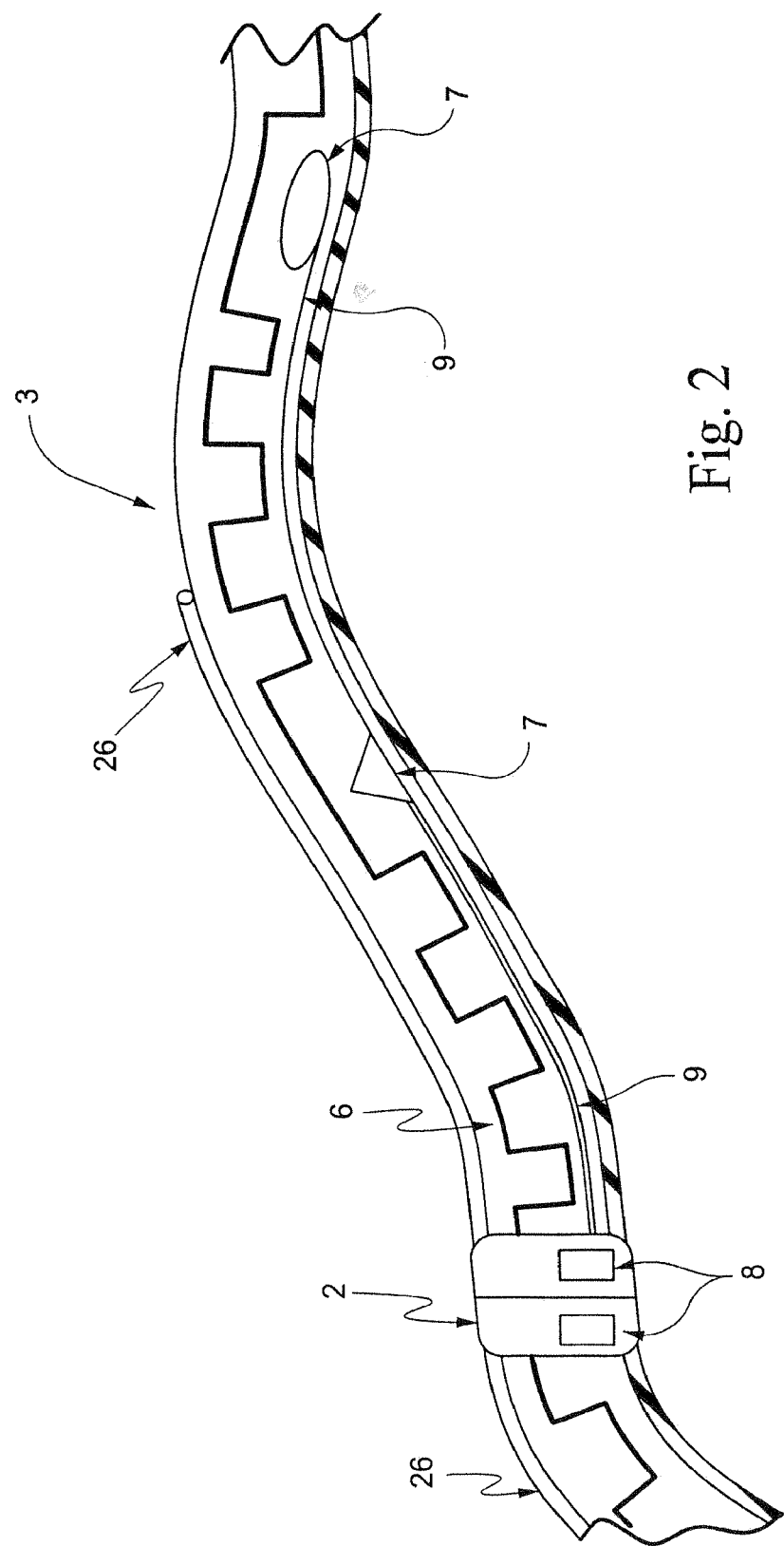
FIG. 2 is a schematic perspective view of another embodiment of the flexible tape heater.

FIG. 2 illustrates one embodiment of the flexible tape heater 3, in which the heating is by a heating element 6.

In one embodiment, the heating element 6 is formed by printed circuit techniques applied to a surface of a flexible substrate such as KAPTON®, silicone rubber, all-polyimide, PTFE. Included in the printed circuit techniques which may be used are etched foil, printing and vacuum deposition techniques.

Another sheet of the substrate material is then laid upon the bottom substrate with the heating element and the two sheets of substrate material adhered or fused together to encapsulate the heating element. The Thermofoil™ range of the type of flexible heaters by Minco of Minneapolis USA, described at www.minco.com, are examples of commercially available strip heaters which may be modified for use in the present invention.

An alternative embodiment to produce a flexible tape heater 3 is to use a laminator, such as a twin silicon roller laminator, to encapsulate a heating element 6, that is in the form of wire or ribbon, within two tapes of polycarbonate film. The resulting tape may for example have dimensions ranging from 1 to 10 mm wide and 0.1 to 1 mm thick. Dimensions of from about 0.2 to 0.5 mm in thickness and about 5 mm wide are usable in the patient conduit 4.

The heating element 6 wire or ribbon may have any suitable transverse cross-section, for example circular, elongate or rectangular. The heating element 6 may for example consist of a resistive conductor.

The arrangement of the heating element 6 between the laminating films may be any ordered or disordered arrangement that increases the heat transfer of the flexible tape heater 3 to the surrounding media, be it gas or liquid. The heating element 6 may also have a positive thermal coefficient (PTC) for resistance such that heating decreases as the temperature increases towards a desired temperature.

Alternatively the heating element 6 may have a negative thermal coefficient (NTC) to allow sensing of the temperature of the heating element 6 or surrounding media.

In other embodiment there may be multiple heating element circuits within the flexible tape heater 3. The multiple heating elements may be connected in series or parallel. The use of these multiple heating circuits within a flexible tape heater 3 enables additional heating to be applied as required in the operation of the respiratory apparatus.

In other embodiments the laminating films may be polyester, polypropylene or any suitable and approved substance for respiratory medicine use. Alternatively, multiple laminating films may be used to create a composite strip having the desired properties while retaining the desired compatibility of the outer film for respiratory medicine use. Other conductors may also be present between each of these multiple layers, for example so as to form multiple heating circuits, such as to allow multiple heating zones along the length of the tape heater.

In another embodiment, a sensor 7 for air temperature, such as a thermocouple, platinum resistance thermometer or thermistor with its attendant signal wires 9, may be included between the two sheets of polycarbonate film. The sensor tip may be flat with a thickness of less than about 2 mm, and may be less than 1 mm Other circuit components such as surface mount circuit components may be incorporated onto the substrate film for sensing and/or controlling and hence into the flexible tape. Also, the heating element 6 and other circuit components can exist in multiple layers separated by substrate films as described above.

For the flexible tape heater 3 the other circuit components all have the common physical feature that they are of a small enough dimension to enable them to be accommodated in the overall profile of the flexible tape heater 3 and collocated with the heating element 6.

In an alternative embodiment the flexible tape may not have a heater element 6, but instead incorporate one or more other circuit components for sensing and controlling. Thus a respiratory apparatus may contain two or more flexible tapes, one or more undertaking a heating function and one or more undertaking a sensing and/or controlling function.

The range of other circuit components that may be used is shown by way of example in the following:

Relative and absolute humidity sensors 7a;

Temperature sensors 7a with a positive temperature coefficient (PTC) or negative temperature coefficient (NTC) in the form of a thermistor or alternatively the PTC property may be intrinsic to the heating element 6 so that the flexible tape heater 3 is self limiting;

Thermocouples, platinum resistance thermometers and the like may be used to produce an actual temperature value signal for control and monitoring;

Directional flow sensing of the gas may realized by using at least two independently controlled heating sections spaced along the flexible tape heater each comprising a temperature sensor (e.g. thermistor). The two or more heating sections are controlled and the temperatures sensed to detect the direction of gas flow;

Hot wire anemometry for gas flow sensing 7a;

Ambient pressure sensing 7a, e.g. inspiratory versus expiratory pressures;

Controller 7b that makes use of the output from a sensor 7a, such as for temperature, to control, for example, a transistor which regulates the current applied to a heating element 6 used for the heating element(s);

Identification-Communication-Memory chips 8 which enable identification and communication of the operating parameters of the flexible tape heater 3 to the base unit 22, other heaters and components in the respiratory apparatus. For example, the flexible tape heater 3 may communicate regarding itself as well as detect and report regarding other components that are attached to the respiratory apparatus such as the patient mask 5 type or the patient conduit 4 type or an active vent system. The information thus gathered by the flexible tape heater 3 may then be sent to the base unit 22. The identification-communication-memory system may consist of in part a radio frequency identification chip (RFID) to store the heater 6 and sensor 7a identification and operating parameters. The base unit 22 may have a capability to communicate with the RFID chip and adjust its operation accordingly. Such a system has been described in the Australian Patent Application No. 2005907200, titled "Identification System and Method for Mask and Ventilator Components," the entire contents of which are incorporated herein by reference. The communication may also be used to control an active vent system;

Electromagnetic communication protocols via miniature aerials and receivers, e.g. "Bluetooth.". Aerials for transmitting and receiving information may be located for example in the flexible tape heater 3, the wall of the patient conduit 4, or an active vent system, or within the other components of the respiratory apparatus as illustrated in FIG. 5. In another embodiment the aerials could be of a dimension as allowed by the length of the flexible tape heater 3 or the patient conduit 4;

Power supply to the flexible tape heaters may be in a similar manner to the electromagnetic communication described above. In this embodiment the aerials or inductive coils would be adapted for power transmission.

These components can be located anywhere along the flexible tape heater 3 as appropriate to their function. For example, a thermocouple may be located on the flexible tape heater 3 at the end adjacent the patient mask 5 to enable closed loop temperature control based on gas temperature delivered to the patient mask 5.

In an alternative embodiment the temperature sensor may be located in or in the vicinity of the patient mask 5 but separated from the flexible tape heater 3. However the temperature sensor may communicate with the flexible tape heater 3 in the one of the manners described above to enable closed loop control of the temperature of the gas delivered to the patient.

The flexible tape heater 3 may also comprise microtubes 26 (FIG. 2) to allow remote sensing away from the flow generator and/or humidification chamber 1. The microtubes may, for example, provide pressure, noise/snore and/or cardiological signal sensing. For example, the microtubes may be attached to the side of the flexible tape heater 3 and connected back to the flow generator 20 in one of the manners described above. The use of microtubes 26 provides the benefit of avoiding flow noise within the patient conduit 4 and other areas in the respiratory apparatus.

The sensing and control methods described above allow closed loop control to be used for improving gas delivery to the patient mask 5 so that it is at the desired temperature and humidity. Alternatively, a simple open loop system may be used where driving voltages or currents for the heating element may be, for example, from 0.1 to 24 V direct current or the power equivalent for alternating current, that may for example be from 0.1 to 50 W. The sensing and control may also control the level of intentional gas leak from an active vent system, depending on the amount of pressure being supplied. For example, as the ventilator pressure increases the active vent system may be controlled to reduce the level of its intentional leak to an acceptable level.

Additionally, the sensors 7a can be used for compliance or statistical data gathering.

Furthermore, the different components of the heater and/or sensing/control system described herein may be used as stand alone components in a respiratory apparatus not employing a humidifier, and such arrangements are within the scope of the invention.

A flexible tape heater 3 as thus described would be easily removable from the patient conduit 4 to enable cleaning, maintenance or replacement. The flexible tape heater 3 also offers efficient heating with sensing and control components 7 being easily incorporated into the flexible tape heater 3.

Floating Heater

Figures 3, 37B:
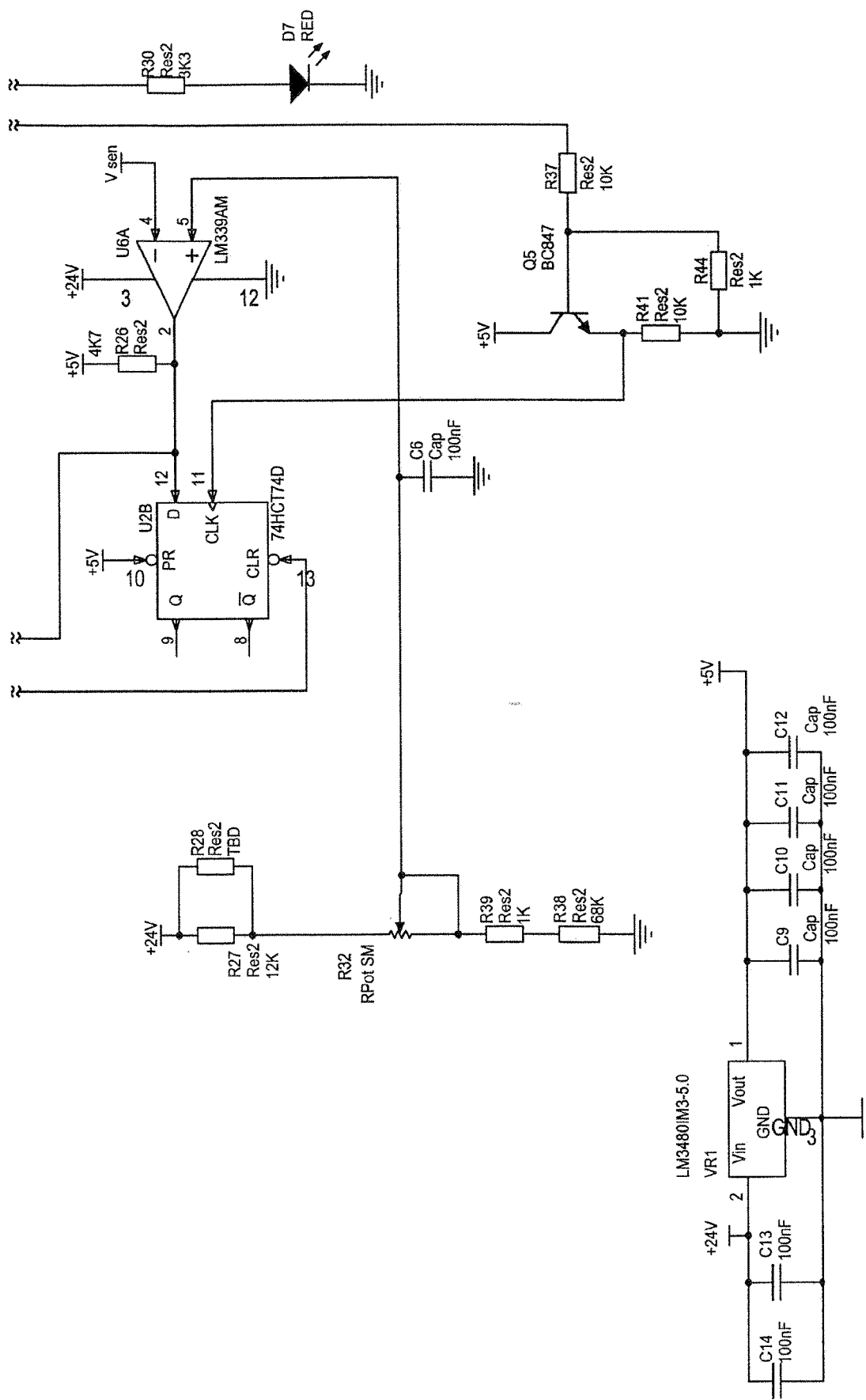

In FIG. 3 a humidifier arrangement utilizing a floating heater 12 is illustrated. The floating heater 12 floats in the body of water 13 in the humidifier chamber tub 1 such that a substantial portion of the floating heater 12 is immersed but is still adjacent the water surface 14 so as to heat that part of the water near the surface 14.

The floating heater 12 may comprise a length of flexible tape heater of similar construction to that discussed above with reference to FIGS. 1-A to 1-C and 2. The end of the heater located in the inlet conduit 10 leading from the flow generator 20 may be provided with a connector 11 which enables the floating heater 12 to connect with a flexible tape heater, where that flexible tape heater is connected to the base unit 22 (FIG. 5) of the respiratory apparatus. The floating heater 12 receives its electrical supply via the upstream end connector 11. Any sensing or controlling signals to or from the floating heater 12 are also received via the upstream end connector 11.

The downstream end 2 of the floating heater, located in the patient conduit 4 leading to the patient interface, may have a further connector for supplying power and any communication with a further portion of flexible tape heater located in the patient conduit 4 (see FIGS. 1-A, 1-B, 1-C and 2).

The heater 12 may be adapted to float either by the natural buoyancy of the heater itself, by surface tension effects, or may be supported in a manner which keeps the heater near the water surface regardless of changes in the water level.

Figures 4, 37B:
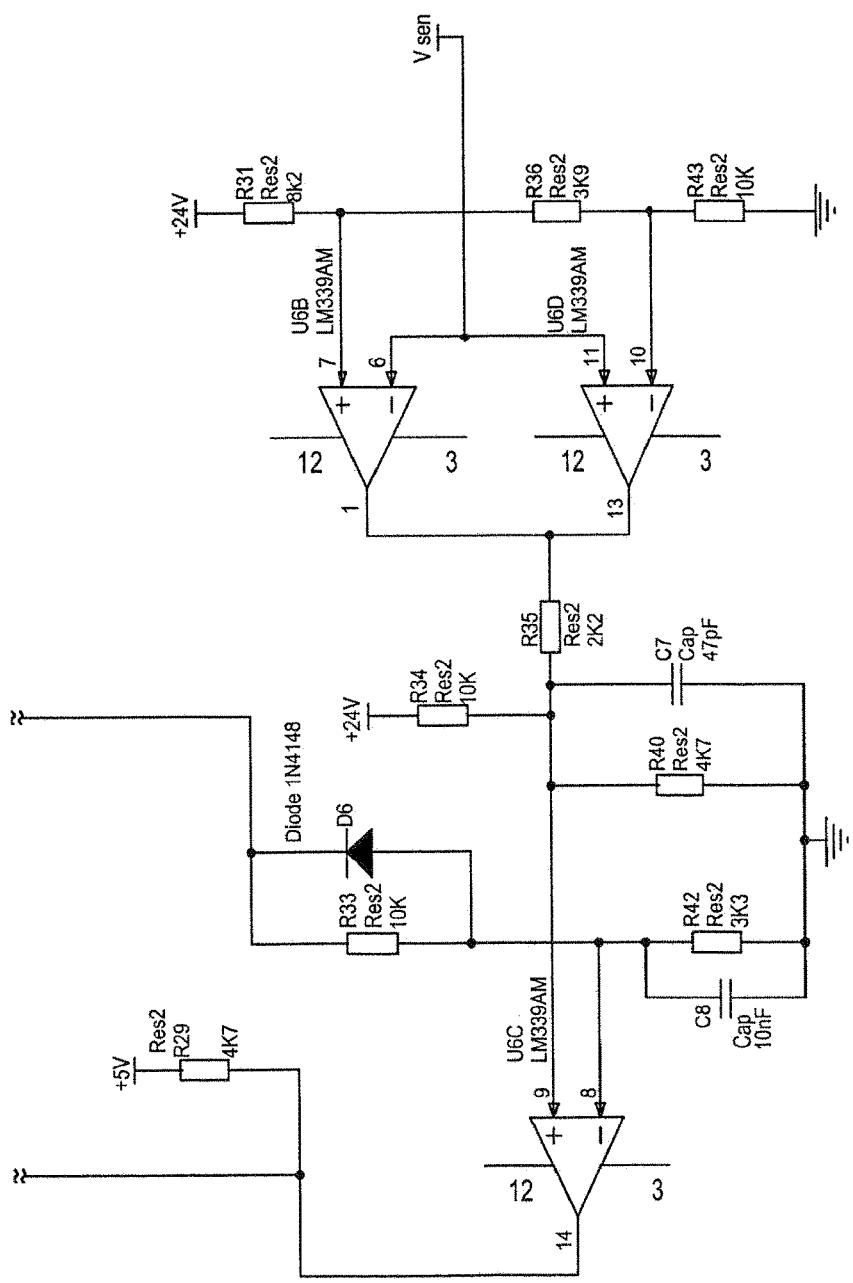

FIGS. 4-A-E illustrate a number of embodiments that the floating heater 3, 12, 16, 17 may have within the humidification chamber 1. The floating heater 3, 12, 16, 17 in each embodiment is formed either from a flexible tape heater of the type previously described or a plate form of the flexible tape heater 3, the floating plate heater 16.

The construction and use of a floating flexible tape heater 3 and the floating plate heater 16 is the same as described for the flexible tape heater 3 above, except that it is applied to water. This has the significant advantage that the heater for both applications is robust to gas or water immersion, since a floating flexible tape heater 3 or a floating plate heater 16 could be partially immersed in water during the respiratory apparatus' operation, either unintentionally as the body of water increases or decreases in volume or by tilting of the device, or intentionally to maintain the temperature of the water vapor in the gas of the humidification chamber 1.

Figure 7:
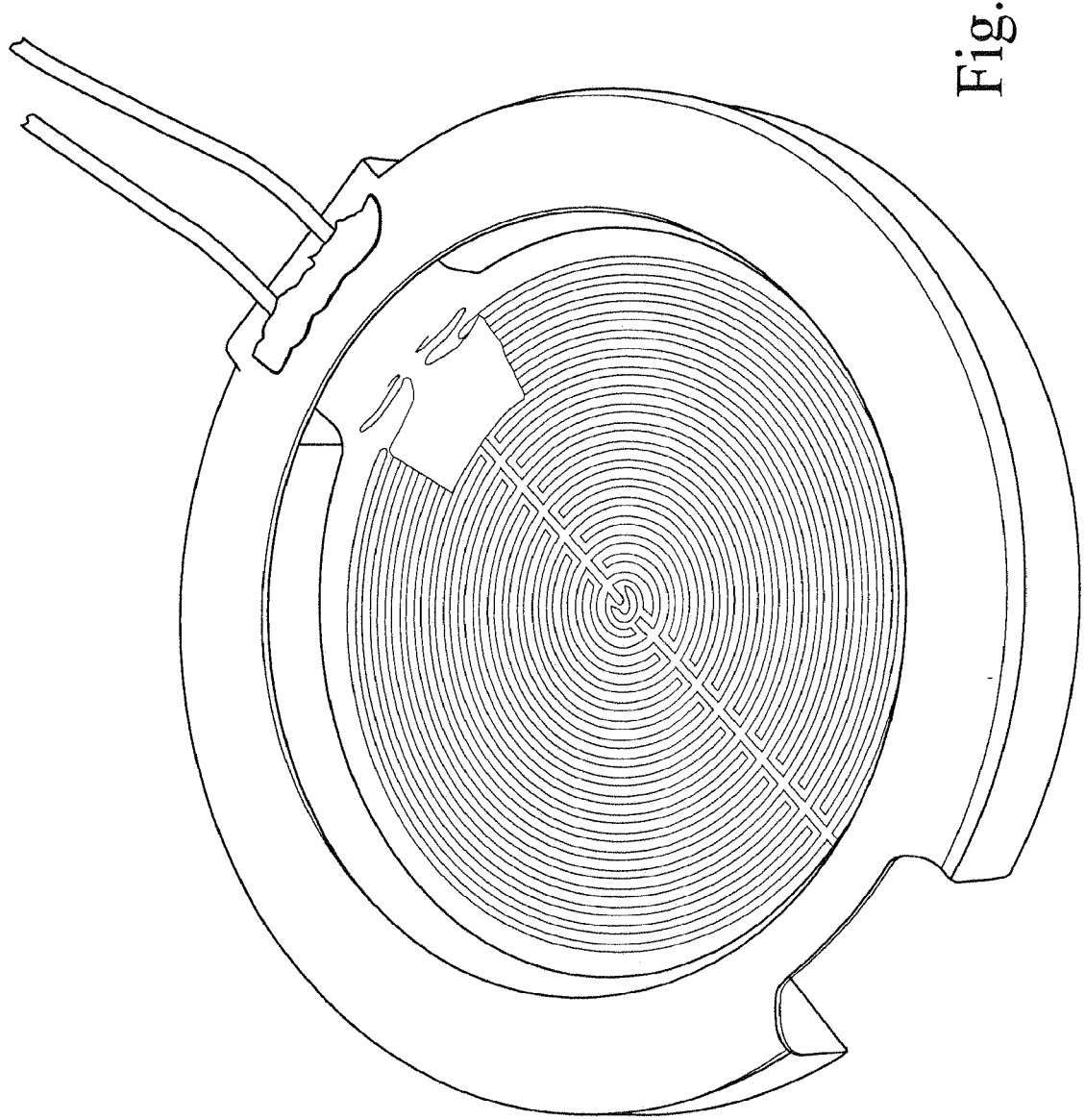
FIG. 7 illustrates the floating heater plate located in a shallow bath that also floats at the water surface of the body of water.

FIG. 4-A illustrates a circular floating plate heater 16 which is secured under a floating support grid or plate 15, for example of a buoyant plastics material. The support grid 15 provides a floating positioning mechanism for the floating plate heater 16 spacing the heater element just below the water surface 14 so that there is sufficient contact with the water to cause vaporization. In an alternative embodiment shown in FIG. 7, the floating heater plate is located in a shallow bath that also floats at the water surface 14 of the body of water 13. In this embodiment the floating plate heater comprises at least one aperture to allow water to fill the bath to cover the heater plate 16. The small volume of water in the bath is rapidly heated to produce vapor.

FIG. 4-B shows another embodiment where the plate form is rippled or dimpled in a regular or irregular fashion. The rippling and/or dimpling provides valleys which allow pockets of water to accumulate on the upper surface of the floating plate heater 16. In this embodiment, the floating plate heater 16 is naturally buoyant, so it can float without the need for a support grid or other buoyancy device.

FIG. 4-C illustrates a flexible tape heater 3 which has been wound into a helix. In this embodiment the floating, helical flexible tape heater 17 can intrinsically float such that a sufficient portion of the floating, helical flexible tape heater 17 is immersed in the body of water 13. In another embodiment the flexible tape heater 3 could be wound in a horizontal spiral, FIG. 4-D. For both the FIGS. 4-C and 4-D embodiments a support grid 15 as used in FIG. 4-A may be used to position the flexible tape heaters 3, 12, 17.

The preceding embodiments for the floating heater 3, 12, 16, 17 represent a number of defined configurations whereas in use the floating heater may assume a combination of the defined or undefined configurations. For example a long helix which continues as a spiral, combining FIGS. 4-C and 4-D.

In the above embodiments of the floating heater 3, 12, 16, 17 the heater provides effective heat transfer to the water surrounding the heater. In addition, the water adjacent to the water surface is heated for vaporization rather than heating the whole body of water from the bottom up as in the case of a heater being located at the bottom of the body of water 13.

Additionally, the flexible tape heater formation may be spiraled or otherwise formed so as to be partly immersed in the body of water 13 so that it heats both the water near the air and the air near the water to produce a stratified zone of heat to improve water uptake for humidification. Thus, the floating heater 3, 12, 16, 17 may be more power efficient in generating water vapor, and more effective in quickly achieving the desired water surface temperature for humidification at start-up of the apparatus.

Multiple Zone Heating

FIG. 5 illustrates a respiratory apparatus which makes use of three heaters that are of the same general construction and use as described for the flexible tape heater 3 and the floating plate heater 12, 16, 17 described above.

The heaters may comprise multiple heating circuits, so that each of the three heater zones may be operated independently.

A flow generator 20 or blower supplies gas supplied from an ambient temperature supply which may be the air in the room or augmented or replaced by a specific gas supply such as oxygen. A pre-heater 18 is located in the blower coupling 10 leading to the humidifier 1. The blower coupling may be rigid, flexible or a conduit as required for the operation of the blower coupling 10 or the operation of the pre-heater 18 located within the blower coupling 10. The pre-heater 18 is connected to the controller/power supply 21, of the base unit 22, which supplies power and communication with any sensing or controlling components 7 of the pre-heater 18, as per the flexible tape heater 3 embodiment. The pre-heater 18 is connected to the floating heater 12, 16, 17 of the humidification chamber 1 at the blower conduit connector end 11. The floating heater 12, 16, 17 receives the controller/power supply 21 power supply and any communication, with the sensing or controlling components 7 of the floating heater 12, 16, 17, via the pre-heater 18.

Alternatively the floating heater 12, 16, 17 may also connect with the controller/power supply 21 via the wall of the blower coupling 10 in the manner described above in relation to FIGS. 6-A and 6-B discussing the patient conduit 4.

The post heater 19 is located in the patient conduit 4. The patient conduit connector end 2 provides the controller/power supply 21 power supply and communication for the sensing and controlling components 7 of the post heater 19. The patient conduit connector end 2 may connect to the controller/power supply 21 via floating heater 12, 16, 17 as shown in FIG. 5 or via the conduit wall 25, as shown in FIGS. 6-A and 6-B, and then via the humidification chamber 1 to the controller/power supply 21 in the base unit 22.

In an alternative embodiment one or more of the heaters may not be of the type described above but another suitable heating element. For example, the pre-heater 18 may be formed as a simple wire heater or other conventional heater type rather than as a flexible tape heater of the type described herein.

The use of such arrangements may give the advantages of:

A single inter-connected heater system which is internal to the blower coupling 10, humidification chamber 1 and patient conduit 4;

The complete heater, sensor and control system can be removed simply for cleaning, maintenance or replacement;

The interconnection facilitates a high degree of closed loop control for temperature and humidity of the gas delivered to the patient;

The ability to sense temperature and humidity at different sections of the patient conduit 4 in order to control the condensation at various sections in the patient conduit 4;

The different components of the heater and/or sensing/control system may be used in combination or separately within a conventional humidifier. For example the flexible heating tape 3 may also be used to heat the patient conduit 4 together with a conventional humidifier with a heating base plate. Alternatively the floating heater 12, 16, 17 or flexible tape heater 3 may be used to heat the body of water 13 in the humidification chamber 1 together with a heated or insulated wall patient conduit 4, as described above; and/or The ability to install multiple heaters in parallel and series at any location of the respiratory apparatus. This may allow, for example, "super heating" during the beginning operation of the respiratory apparatus when the body of water 13 requires time to reach the desired temperature. The temporary extra heating of the air with multiple heater circuits would increase the capacity of the air to take up the cooler water. This may be controlled or profiled in response to the temperature of the water in the body of water 14 to provide the appropriate level of humidity.

For the respiratory apparatus the placement of the three heaters, and the timing and sequence of their use allows the gas comfort features of temperature and humidity to be managed by allowing the separate, staggered production of:

Heating of an ambient gas that has a low absolute humidity;

Water vaporization; and/or

Heating of the gas that has an increased absolute humidity (after the humidification chamber 1).

The following example of use illustrates an advantage in the operation of the sample embodiments described herein.

Patient respiratory gas requires attention to the comfort features of temperature and humidity, in particular in winter and colder climates. In the embodiments, the aim of the system from a cold start-up is to rapidly deliver warm gas initially and then increase humidity over time as the humidifier warms up. This approach allows the patient to receive comfortable warm air closely followed by an increasing relative humidity, before there is an onset of any adverse symptoms of low humidity respiratory assistance.

For a cold start in a winter climate the three heater system may thus operate in the following manner Firstly, the cool ambient temperature gas from the flow generator 20 is warmed by using the pre-heater 18 in the blower coupling 10 with perhaps assistance from the post-heater 19 in the patient conduit 4. This initially provides warm, dry air to the patient.

As the warmed gas flow begins to absorb appreciable water vapor from the unheated water in the humidification chamber 1, the post-heater 19 in the patient conduit 4 would begin or increase its heating in order to prevent "rain-out" condensation in the patient conduit 4. The initial warming of the air with the pre-heater 18 has the advantage of immediately commencing a degree of humidification, as a simple "pass-over" operation, while the floating heater 12, 16, 17 is still warming up the water. The heat for vaporization in the simple "pass-over" operation being provided by the heated air.

As the floating heater 12, 16, 17 begins to warm the water surface and rapidly increase the absolute humidity in the gas passing through the humidification chamber to achieve the desired level of humidification, the post-heater 19 in the patient conduit 4 would adjust its heating to maintain the absolute humidity by preventing condensation in the patient conduit 4. The post-heater 19 may also serve to maintain the desired gas temperature in the patient conduit 4. The pre-heater 18 may have a heating profile based on the level of heating of the body of water 13 in the humidification chamber 1, the heating profile being the rate of heating of the gas flow in a period of time that can be provided by changing the power to the pre-heater 18 or the structural configuration of the pre-heater 18. It is believed that there may be more effective and control of the humidity by controlling the air temperature as opposed to heating the water.

An additional advantage of this sample embodiment is that it allows reduced power consumption at humidification start up so that the respiratory apparatus may be able to be operated by direct current power supply or a portable power supply. Also, satisfactory operation can still be obtained when two or more heaters are multiplexed, one heater is operated at a time but there is cycling in operation between two or more heaters.

Inlet Conduit Connection

Figure 8:
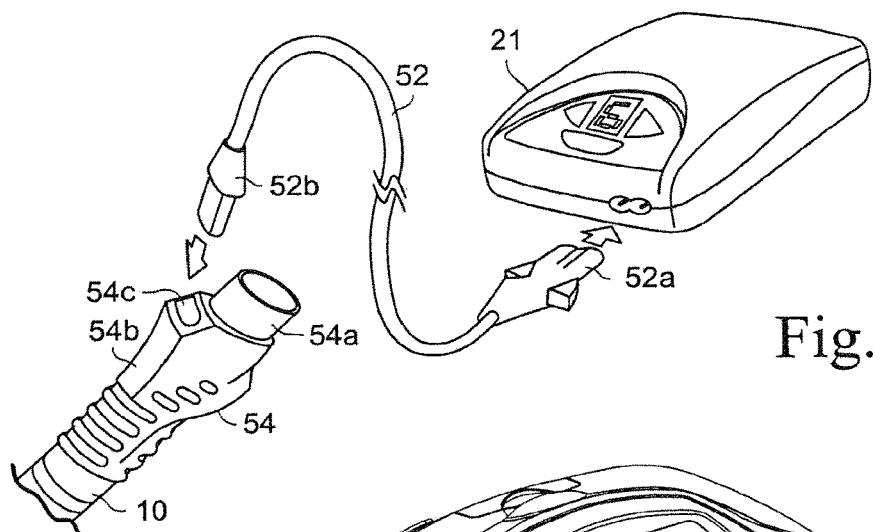
FIG. 8 illustrates a power supply/controller connected to an inlet conduit by a connector according to a sample embodiment of the invention.

Referring to FIG. 8, the power supply/controller 21 may be connected to the inlet conduit/blower coupling 10 by a connector 52. The connector 52 has a first connector 52a connected to the power supply/controller 21 and a second connector end 52b connected to the inlet conduit 10. The inlet conduit 10 has a flow generator cuff or connector 54. The flow generator cuff 54 has an end 54a which is configured for connection with the flow generator 20. The flow generator cuff 54 also has an overmolded grip or cuff 54b which defines a terminal clip 54c.

Figure 9:
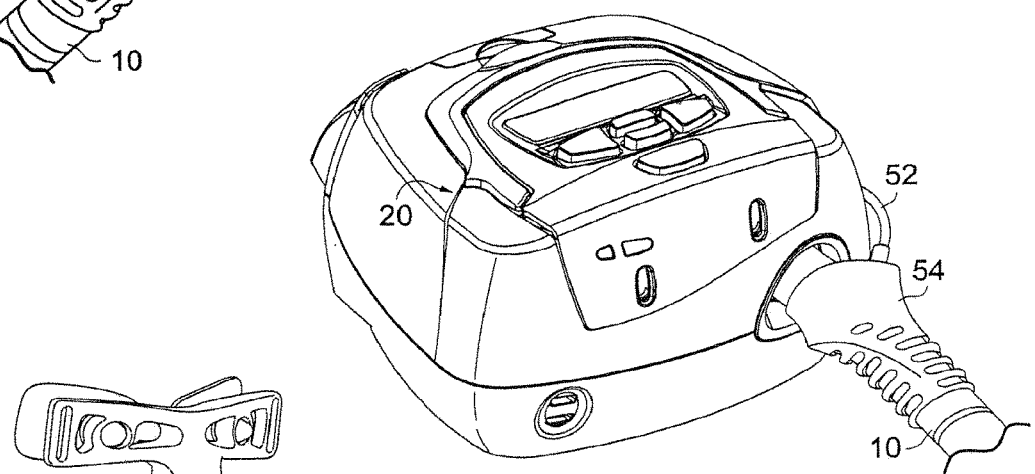
FIG. 9 illustrates the inlet conduit of FIG. 8 connected to a flow generator.

As shown in FIG. 9, the inlet conduit 10 is connected to the flow generator 20 by the flow generator cuff 54. The connector 52 is connected to the flow generator cuff 54 at the terminal clip 54c. Although not shown in FIG. 9, it should be appreciated that the first end 52a of the connector 52 is connected to the power supply/controller 21. The power supply/controller 21 provides electrical current and signals to the flow generator cuff 54 through the connector 52.

Patient Conduit Connection

Figure 10:
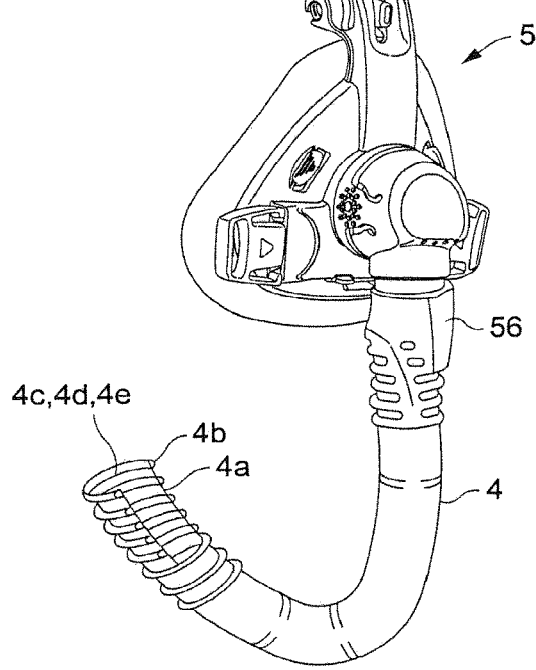
FIG. 10 illustrates a patient conduit or hose according to a sample embodiment of the invention connected to a patient interface.

The patient conduit/air delivery hose 4 is connected to the patient interface 5 by a mask connector or cuff 56, as shown in FIG. 10. The patient conduit 4 includes a tube 4a, for example of thermoplastic elastomer, and a helical rib 4b of very low density polyethylene. Wires 4c, 4d, 4e are supported in the helical rib 4b so as to be in contact with the outer surface of the tube 4a. The wires 4c, 4d, 4e may be used to heat the tube 4a and to carry signals to and from the power supply/controller 21. It should be appreciated that the inlet conduit 10 may have a construction similar to the patient conduit 4, including a tube 10a, a helical rib 10b, and wires 10c-10e supported by the helical rib on the tube.

Inlet Conduit and Flow Generator Connector Cuff

Figure 11:
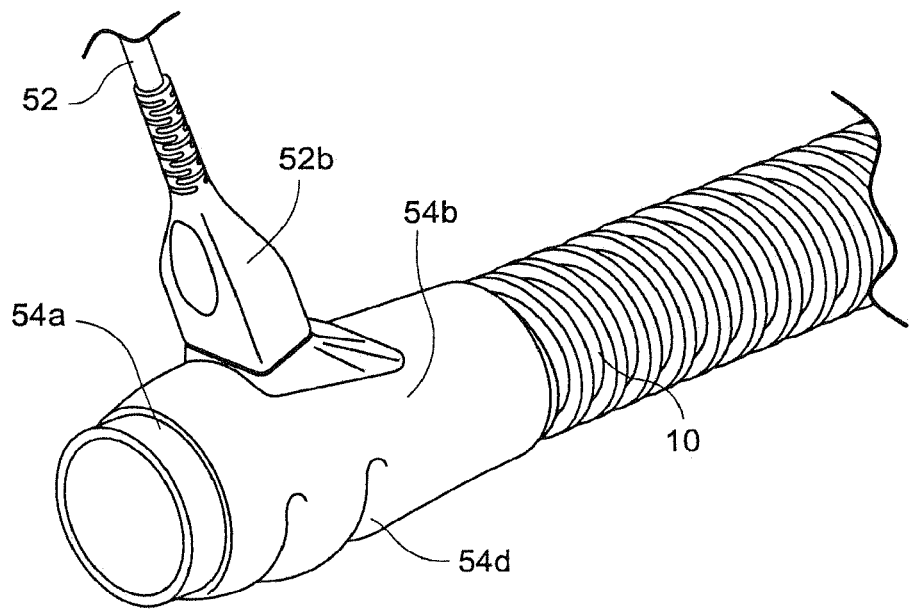
FIG. 11 illustrates an inlet conduit, including a flow generator connector cuff, connected to a connector according to a sample embodiment of the invention.

Referring to FIG. 11, the flow generator cuff 54 includes a connector block 54a. A grip or cuff 54b is overmolded on the connector block 54a to connect the connector block 54a to the inlet conduit 10. The overmolded grip or cuff 54b includes grip features 54d, such as recesses for a user's fingers, in the outer surface of the overmolded grip or cuff 54b to provide a better grip on the connector cuff 54.

Figure 12:
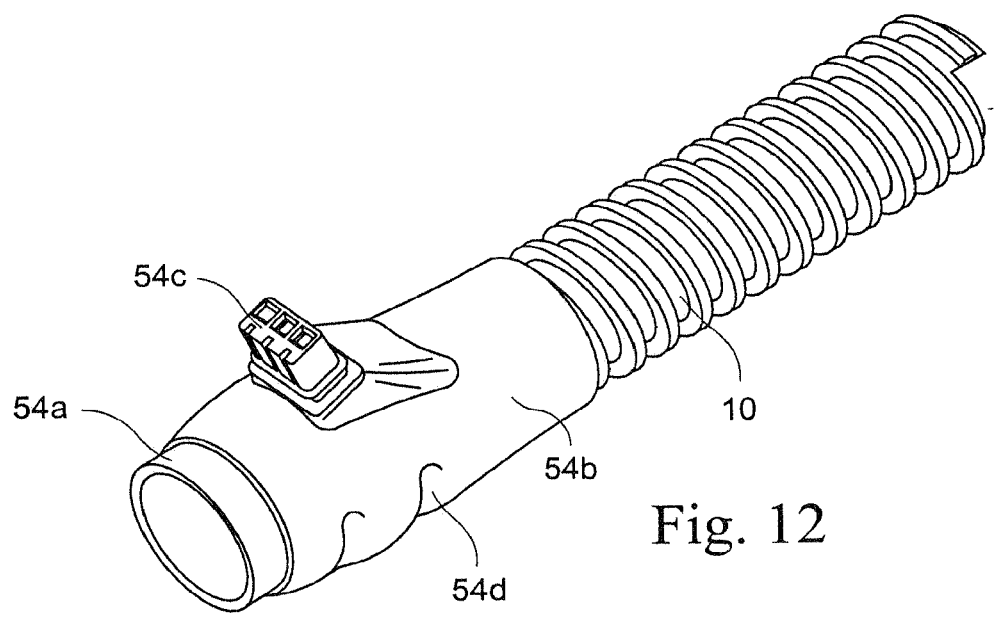
FIG. 12 illustrates the inlet conduit of FIG. 11 disconnected from the connector.
Figure 13:
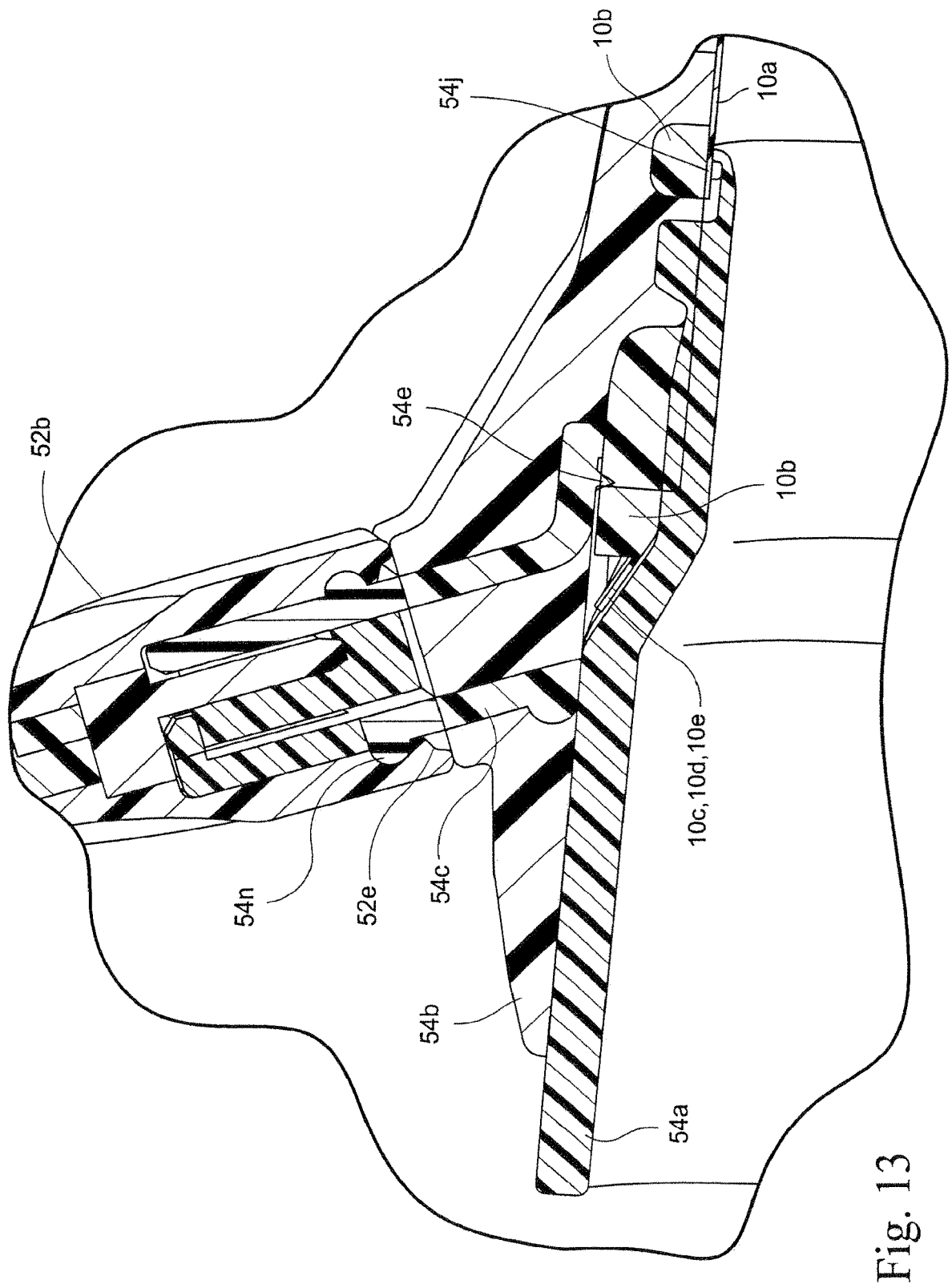
FIG. 13 illustrates a cross section of the inlet conduit and connector of FIG. 11.

As shown in FIGS. 8, 12 and 13, the flow generator cuff 54 includes a terminal clip 54c that receives the second connector end 52b of the connector 52. As shown in FIG. 13, the terminal clip 54c includes a rib 54n that is received in a lead-in 52e of the connector 52. The rib 54n engages the lead-in 52e to secure the connector 52 to the terminal clip 54c.

The terminal clip Mc also includes a tooth Me that locates the wires 10c, 10d, 10e of the inlet conduit 10. The wires 10c, 10d, 10e are placed on the outer surface of the thermoplastic elastomer tube 10a and held in place on the outer surface by the helical rib 10b.

A channel 54j is provided in the connector block Ma to allow the overmolded material 54b to flow and bond to the inside of the tube 10a to establish the connection between the connector block Ma and the inlet conduit 10. The connector block 54, the tube 10a and the overmolded material 54b may be formed of materials that will chemically bond.

Figure 14:
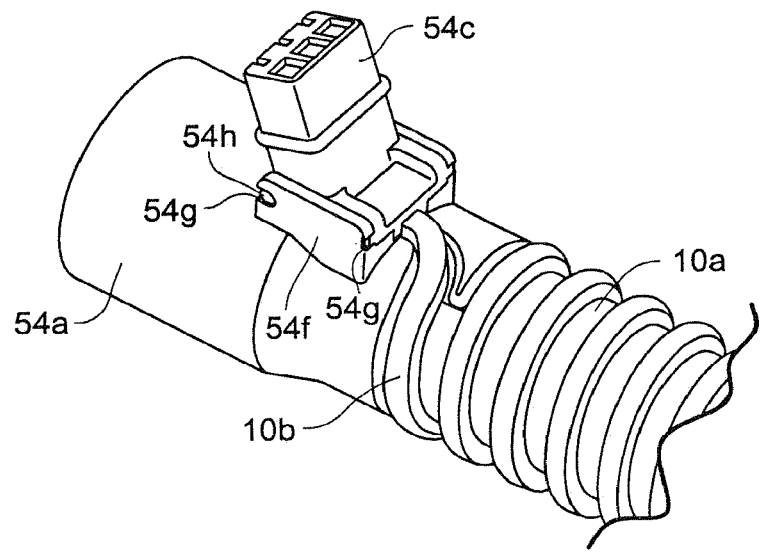
FIG. 14 is a rear perspective view of the inlet conduit and portions of the flow generator connector cuff with the terminal clip connected thereto.
Figure 15:
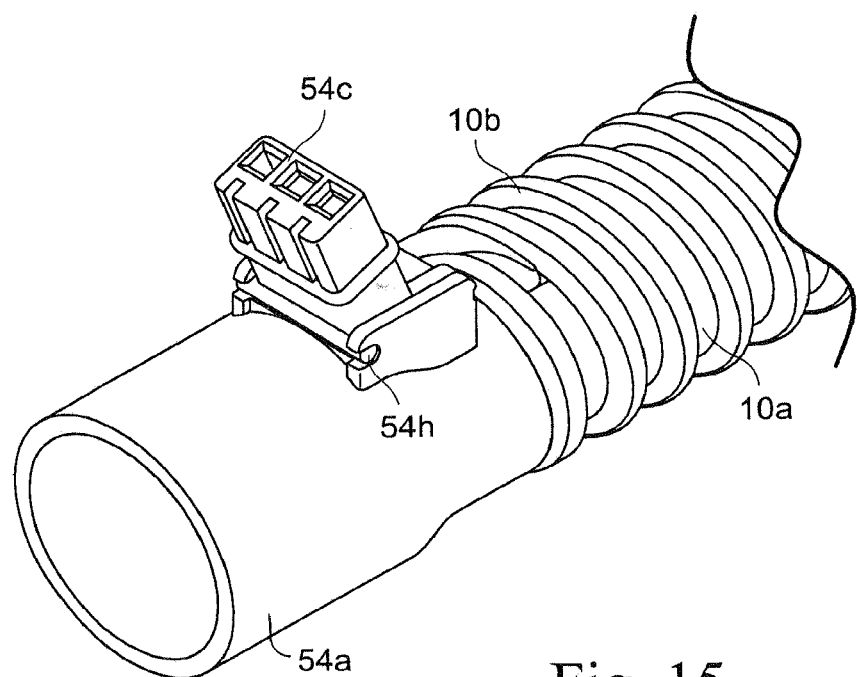
FIG. 15 is a front perspective view of the inlet conduit, flow generator connector cuff portions, and terminal clip of FIG. 14.
Figure 16:
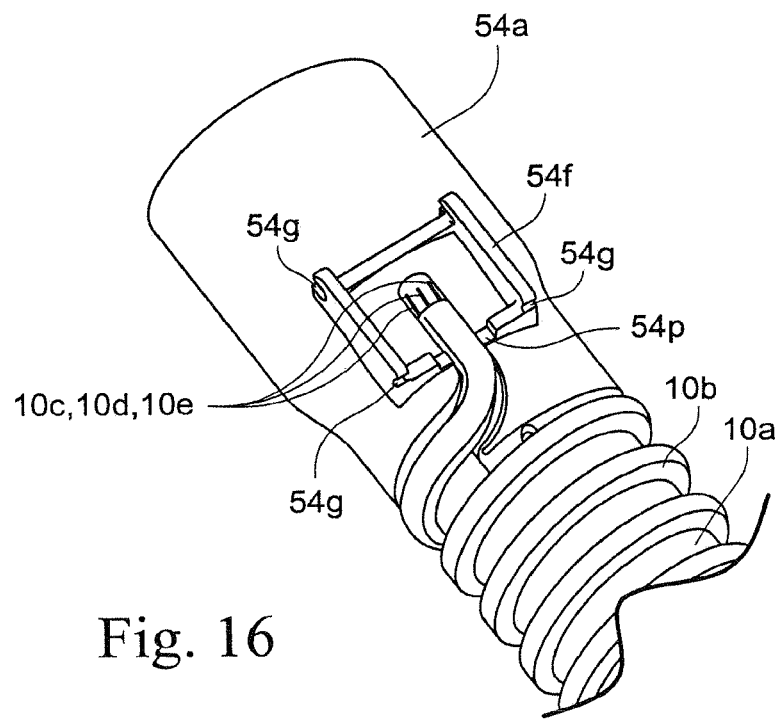
FIG. 16 is a top perspective view of the inlet conduit and flow generator connector cuff portions without the terminal clip.
Figure 17:
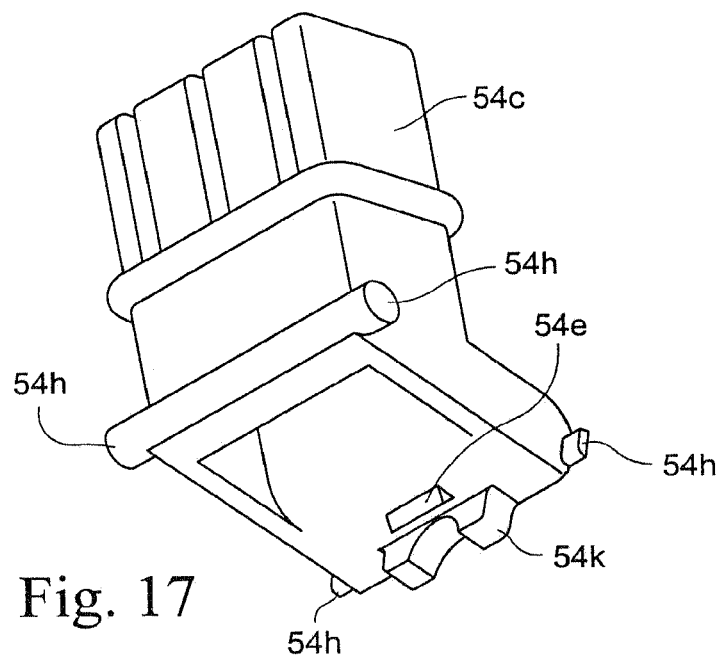
FIG. 17 is a perspective view of the terminal clip according to a sample embodiment of the present invention.

Referring to FIG. 14, the terminal clip 54c includes terminal clip pins 54h that are received in hinged slots 54g of a terminal clip hinge 54f. The terminal clip hinge 54f is provided on the connector block 54a. The terminal clip 54c is snap-fit into the terminal clip hinge 54f to ensure connection of the tooth 54e with the wires 10c, 10d, 10e of the inlet conduit 10. As shown in FIG. 15, the terminal clip 54c may be attached to the connector block 54a prior to attachment of the inlet conduit 10 to the connector block 54a. The terminal clip pins 54h are attached in the hinge slots 54g and the terminal clip 54c is tilted or rotated forward. The inlet conduit 10 is then attached to the connector block 54a and the terminal clip 54c is then rotated or pivoted back so that the tooth 54e contacts the wires 10c, 10d, 10e of the inlet conduit 10. As shown in FIGS. 16 and 17, the connector block 54a includes a guide away 54p for the helical rib 10b of the inlet conduit 10 to position the wires 10c, 10d and 10e for contacting by the tooth 54e.

Figure 18:
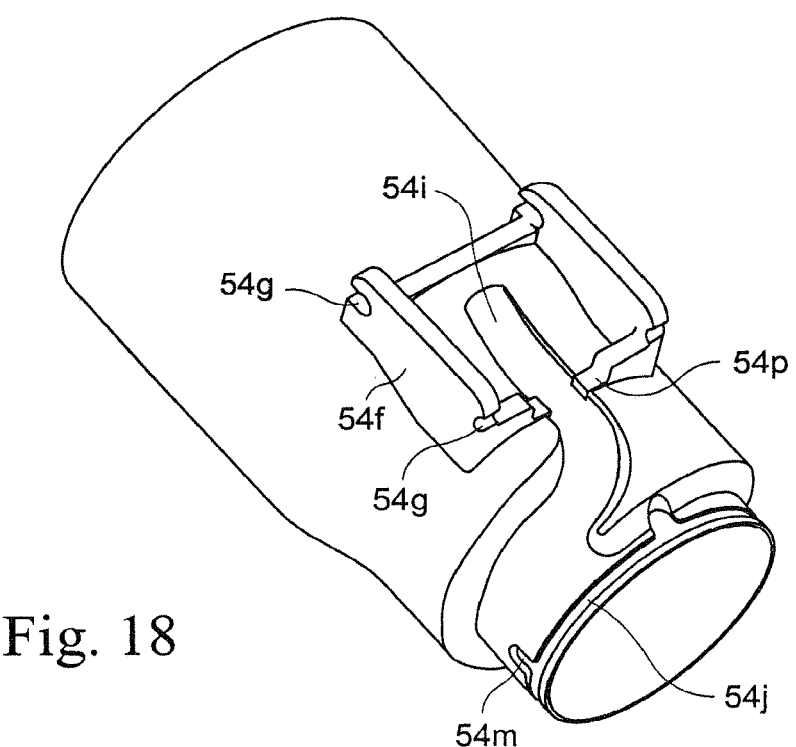
FIG. 18 is a perspective view of the connector block of the flow generator connector cuff according to a sample embodiment of the invention.

Referring to FIG. 17 the terminal clip 54c includes an arched portion 54k that defines a channel with the guide way 54p (FIG. 16) when the terminal clip 54c is inserted into the terminal clip hinge 54f. A groove 54i (FIG. 18) is provided in the connector block 54a to receive the helical rib 10b and the wires 10c, 10d, 10e of the inlet conduit 10. The groove 54i has a smooth surface and wide contact area to prevent or minimize damage to the wires 10c, 10d, 10e. As also shown in FIG. 18, a void 54m is provided adjacent to the channel 54j to allow for the passage of any air during the overmolding of the grip or cuff 54b to the connector block 54a.

Figure 19:
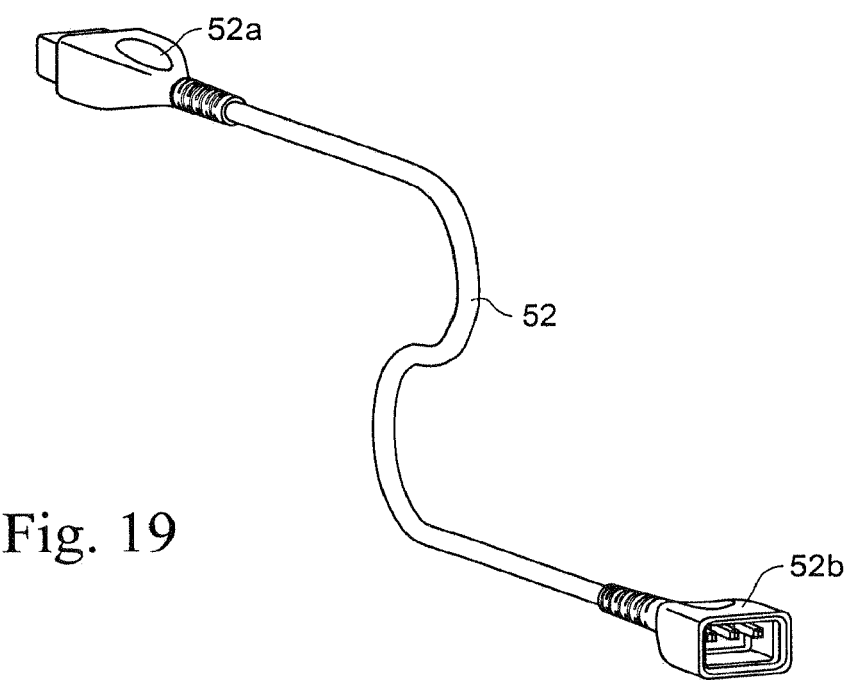
FIG. 19 is a perspective view of the connector according to a sample of the invention.
Figure 20:
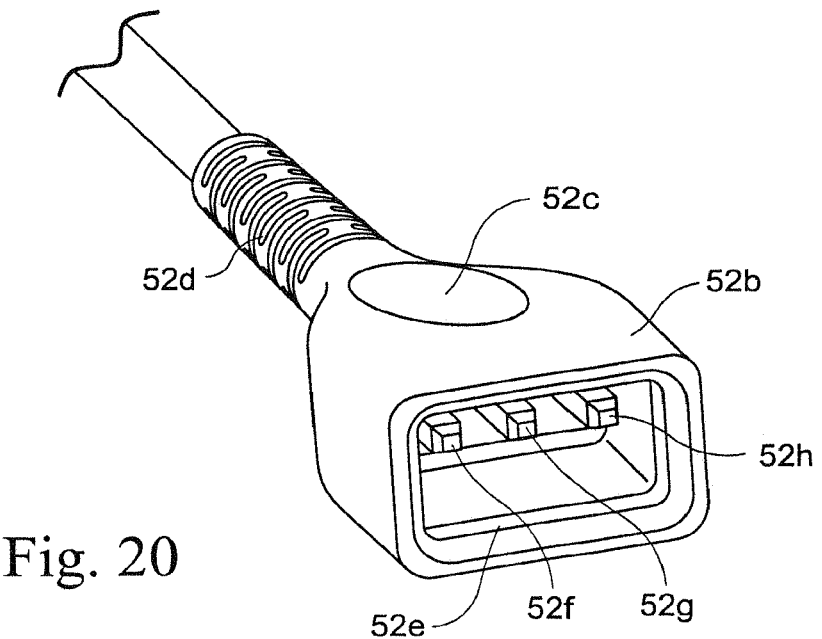
FIG. 20 is a perspective view of the contacts of the connector of FIG. 19.
Figure 21:
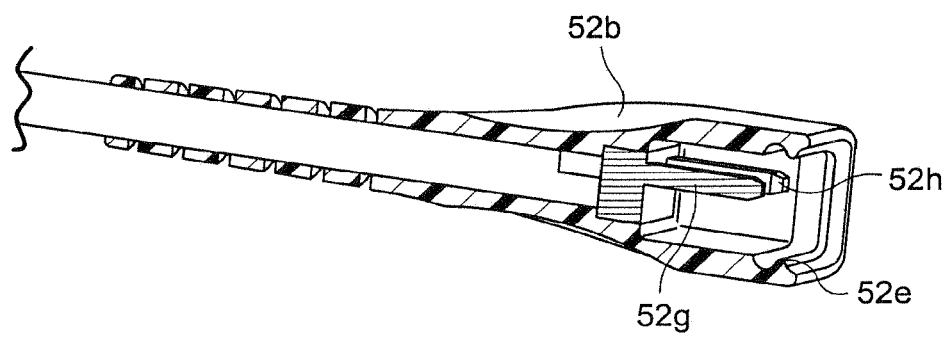
FIG. 21 is a cross section of the contacts and the connector of FIG. 20.
Figure 22:
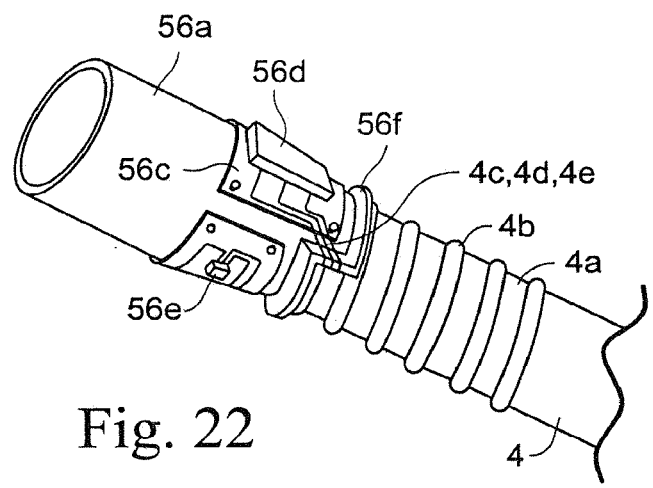
FIG. 22 is a perspective view of the patient conduit or hose and portions of the mask cuff or connector according to a sample embodiment of the invention.

Referring to FIGS. 19-21, the second connector end 52b has a grip feature 52c to permit easier gripping of the second connector end 52b. Strain relief features 52d are also formed in the second connector end 52b to increase flexibility. The grip and strain relief features may also be provided to the first connector end 52a of the connector 52.

Contacts 52f, 52g, 52h are provided for sending and receiving signals from the wires 10c, 10d, 10e of the inlet conduit 10. Although the inlet conduit 10 is shown as including three wires and a terminal clip Mc is shown as having three terminals for receipt of the three contacts of the second connector end 52a, it should be appreciated that any number of wires, terminals and contacts may be used for the delivery and receipt of signals from the power supply/controller 21 to the inlet conduit 10.

Patient Conduit and Mask Connector Cuff

Referring to FIGS. 22-34, a mask connector or cuff 56 is provided for the connection of the patient conduit/air delivery hose 4 to the patient interface 5. The mask connector or cuff 56 includes a connector block 56a that is connected to the patient conduit 4 by an overmolded grip or cuff 56b. The connector block 56a, the tube 4a and the overmolded cuff 56b may be formed of materials that will chemically bond.

Figure 24:
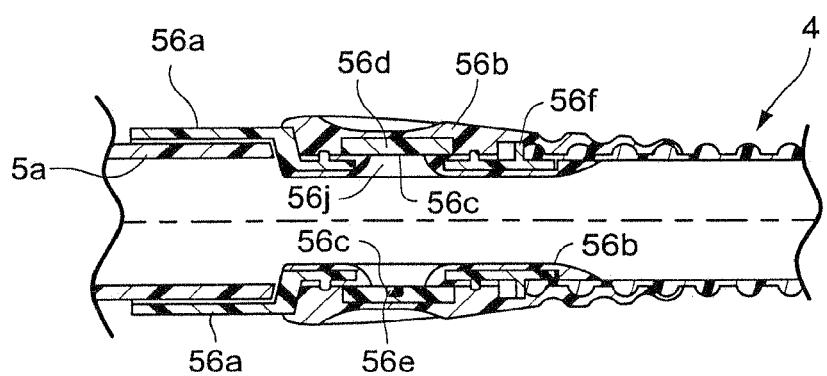
FIG. 24 is a cross section of the patient conduit and mask cuff of FIG. 10.

As shown in FIG. 24, the connector block 56a is connected to an inlet 5a of the patient interface 5. The inlet 5a may be, for example, the swivel elbow of a mask.

Figure 23:
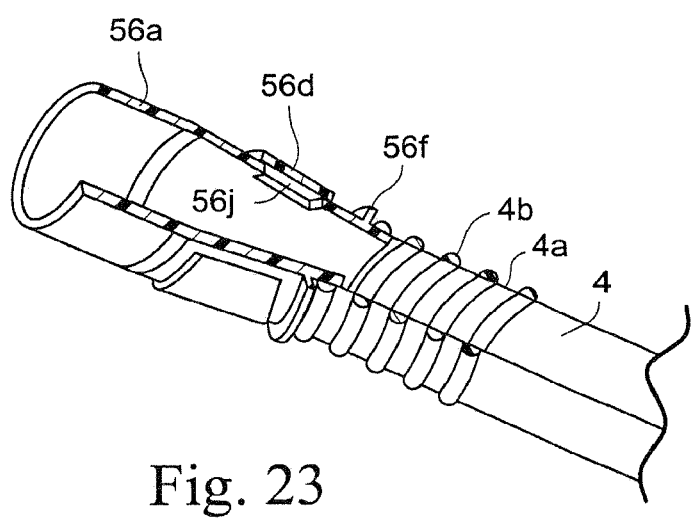
FIG. 23 is a cross section of the patient conduit and mask cuff of FIG. 22 with portions of the cuff removed.
Figure 25:
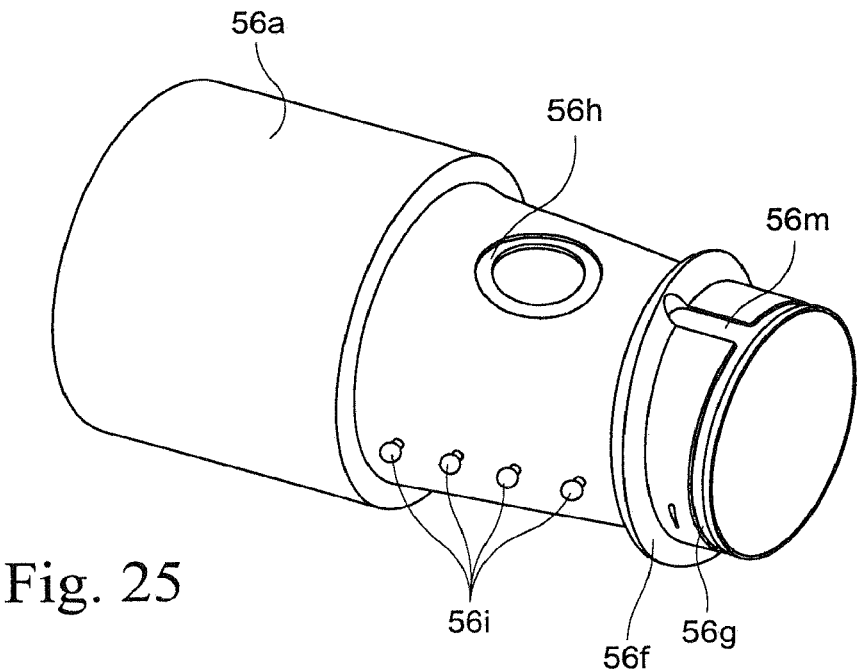
FIG. 25 is a top perspective view of the connector block of the mask cuff according to a sample embodiment of the invention.
Figure 26:
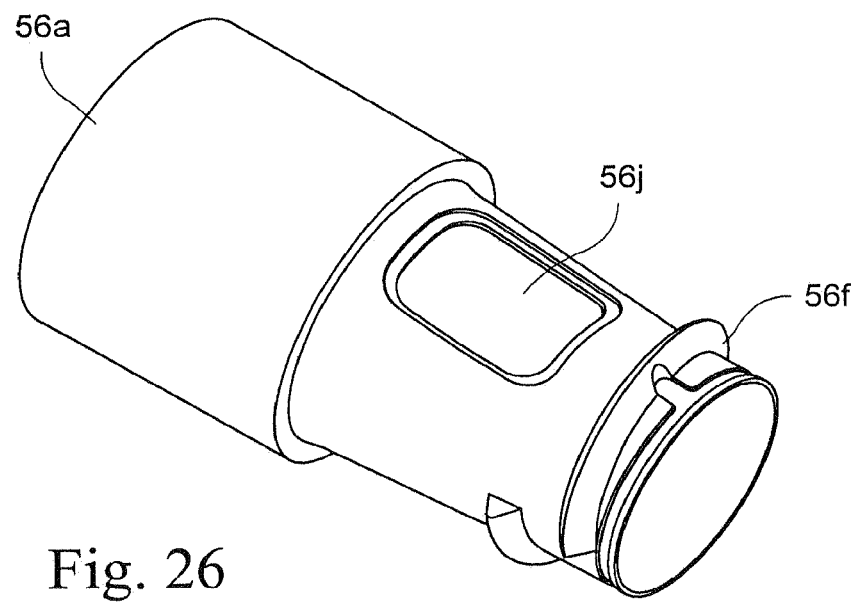
FIG. 26 is a bottom perspective view of the connector block of FIG. 25.
Figure 27:
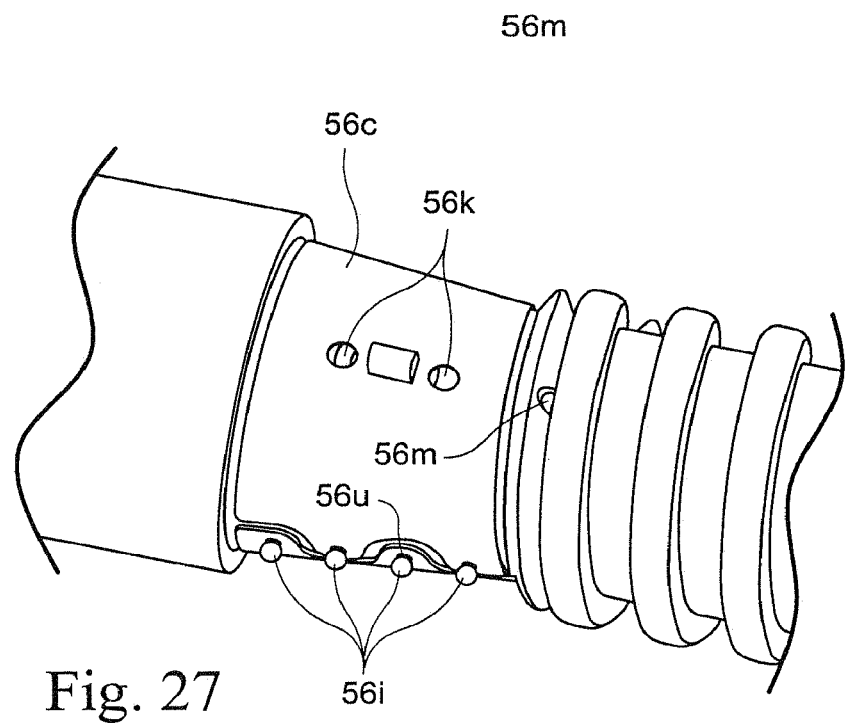
FIG. 27 is a top perspective view of the connector block of the mask cuff in connection with the patient conduit and including a printed circuit board of the mask cuff according to a sample embodiment of the invention.
Figure 28:
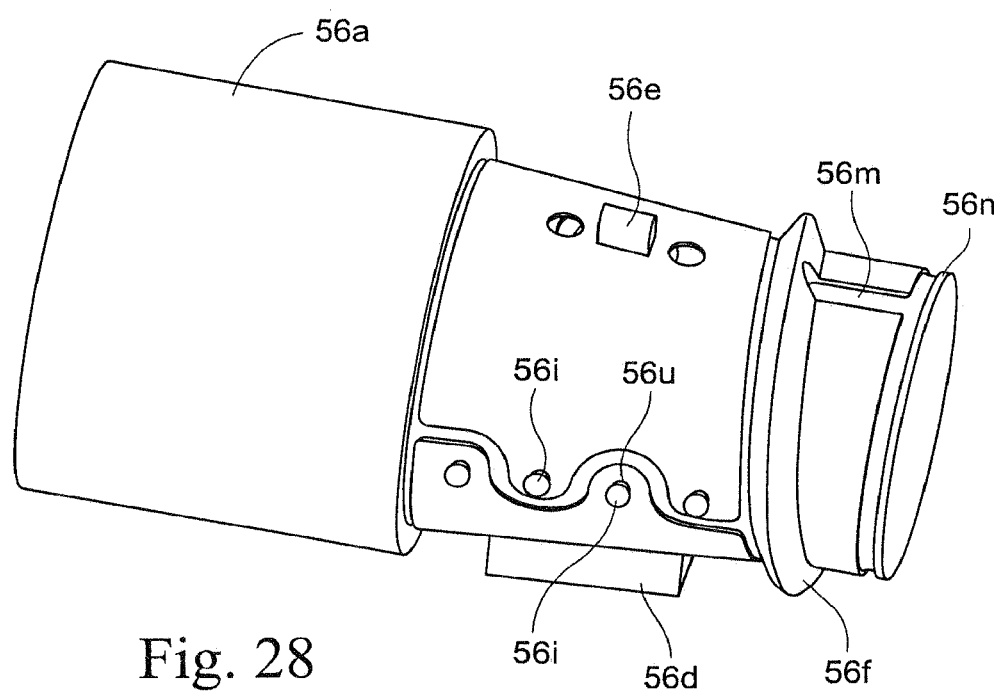
FIG. 28 is a side perspective view of the connector block of FIG. 27 disconnected from the patient conduit.

A printed circuit board (PCB) 56c is provided around the outer surface of the connector block 56a. The wires 4c, 4d, 4e of the patient conduit 4 are attached to the PCB 56c. As shown in FIGS. 25, 27 and 28, the connector block 56a includes snaps or pins 56i that engage holes or apertures 56u in the PCB 56*c*. The PCB 56*c* is thus wrapped around an outer surface of the connector block 56*a* and held in place. A thermal fuse 56*d* and a temperature sensor 56*e*, for example a thermistor, are provided on the PCB 56*c*. As shown in FIGS. 23 and 26, one or more windows 56*j* are provided in the outer surface of the connector block 56*a* where the thermal fuse 56*d* and the temperature sensor 56*e* are provided. The windows 56*j* are covered by the PCB 56*c*, as shown in FIG. 24. As discussed in more detail below, the PCB 56*c* includes a heater track that is cooled by exposure of the PCB 56*c* to the airflow along the window 56*j*.

Figure 29:
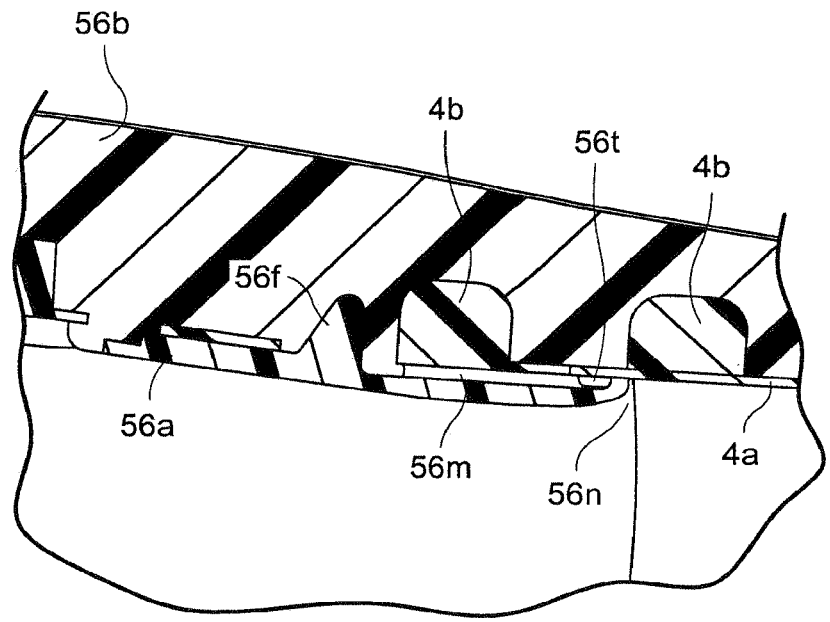
FIG. 29 is a cross section of the patient conduit and connector block of FIG. 27.

A helical rib 56*f* is provided on the outer surface of the connector block 56*a* to locate the patient conduit 4, as shown in FIGS. 22-26. As shown in FIG. 25, the outer surface of the connector block 56*a* includes a stepped recess 56*h* to allow the overmold material to flow and bond to the underside of the flexible PCB 56*c*. As shown in FIG. 29, the connector block 56*a* also includes a channel 56*t* to allow the overmold material to bond with the inside of the tube 4*a* of the patient conduit 4. Referring back to FIG. 25, a void 56*g* is provided adjacent the channel 56*t* to allow for the escape of air during overmolding. As also shown in FIGS. 28 and 29, the end of the connector block 56*a* includes a profile 56*n* that minimizes the capacity for debris to collect and to be cleaned if debris does collect. The end of profile 56*n* also minimizes flow impedance of the overmolded material.

Figure 30:
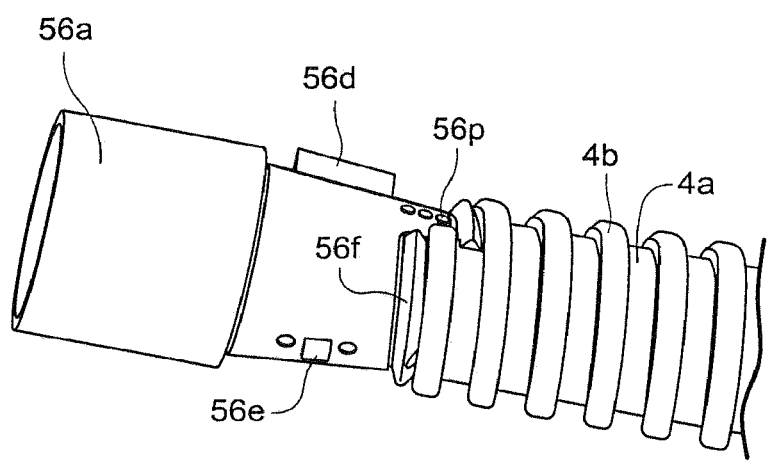
FIG. 30 is a perspective view of the patient conduit and the connector block of the mask cuff according to a sample embodiment of the invention.

As shown in FIGS. 25 and 27, an access channel 56*m* is provided between the helical rib 56*f* and the end channel 56*t* to allow the overmold material to bond the tube 4*a* to the connector block 56*a*. As shown in FIG. 30, the tube 4*a* is twisted on to the connector block 56*a* and the wires 4*c*, 4*d*, 4*e* of the patient conduit 4 are soldered to the flexible PCB 56*c* as shown at 56*p*.

Figure 31:
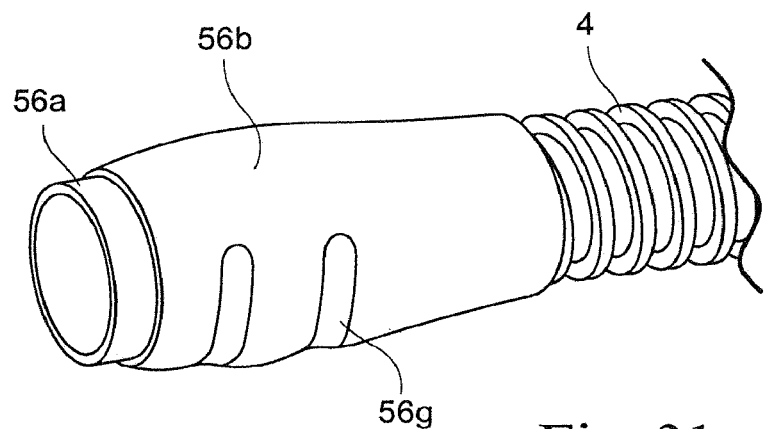
FIG. 31 is a perspective view of the patient conduit and mask cuff according to a sample embodiment of the invention.
Figure 32:
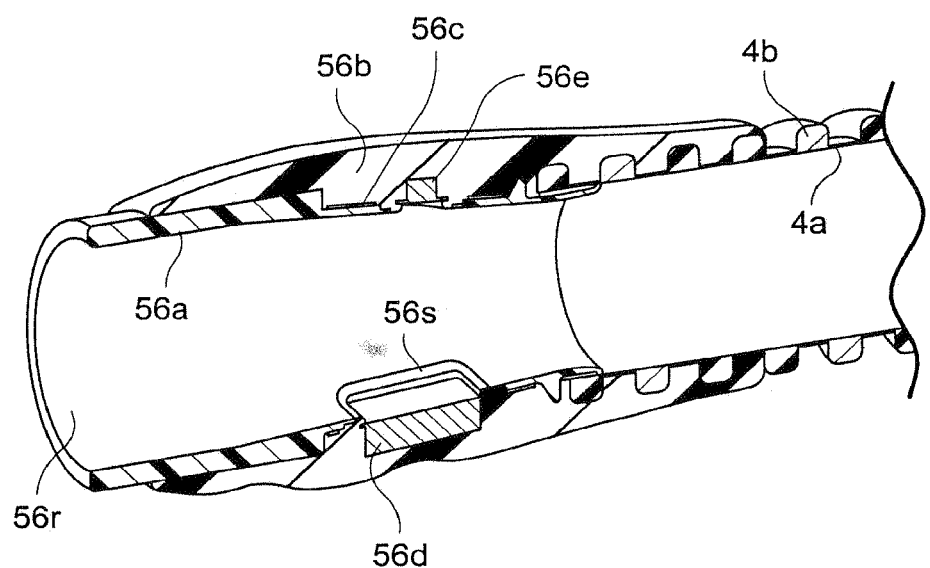
FIG. 32 is a cross section of the patient conduit and mask cuff of FIG. 31.

Referring to FIG. 31, the overmolded grip or cuff 56*b* may include a molded grip feature 56*q*, such as recesses to accommodate a user's fingers, to improve the gripping ability of the mask cuff or connector 56. The connector block 56*a* may be formed of a rigid polymer and the overmolded grip or cuff 56 may be formed of a thermoplastic elastomer. As shown in FIG. 32, the connector block 56*a* may have a standard 22 mm ISO taper for connection to the patient interface. As also shown in FIG. 32, the overmolded material may be blanked off at 56*s* in the region of the thermal fuse 56*d*.

Figure 33:
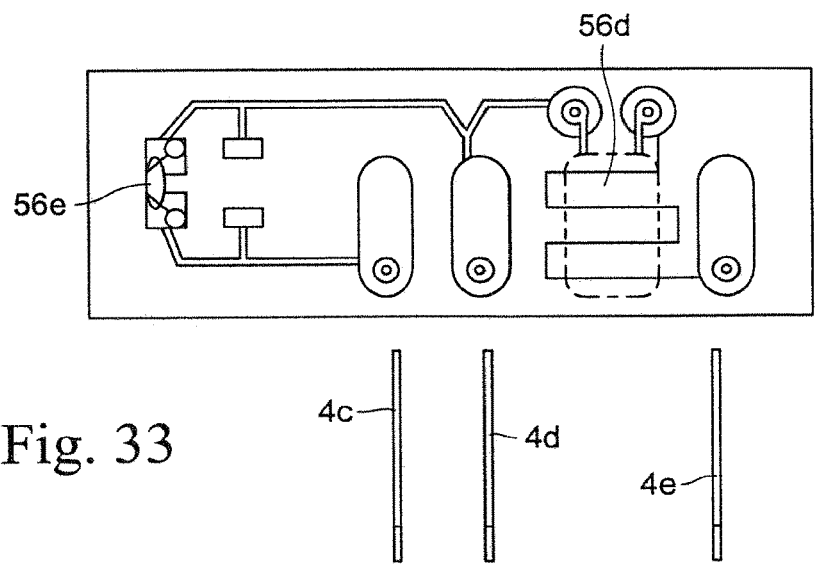
FIG. 33 is a schematic illustration of the temperature sensor and thermal fuse of the circuit of the mask cuff according to a sample embodiment of the invention.
Figure 34:
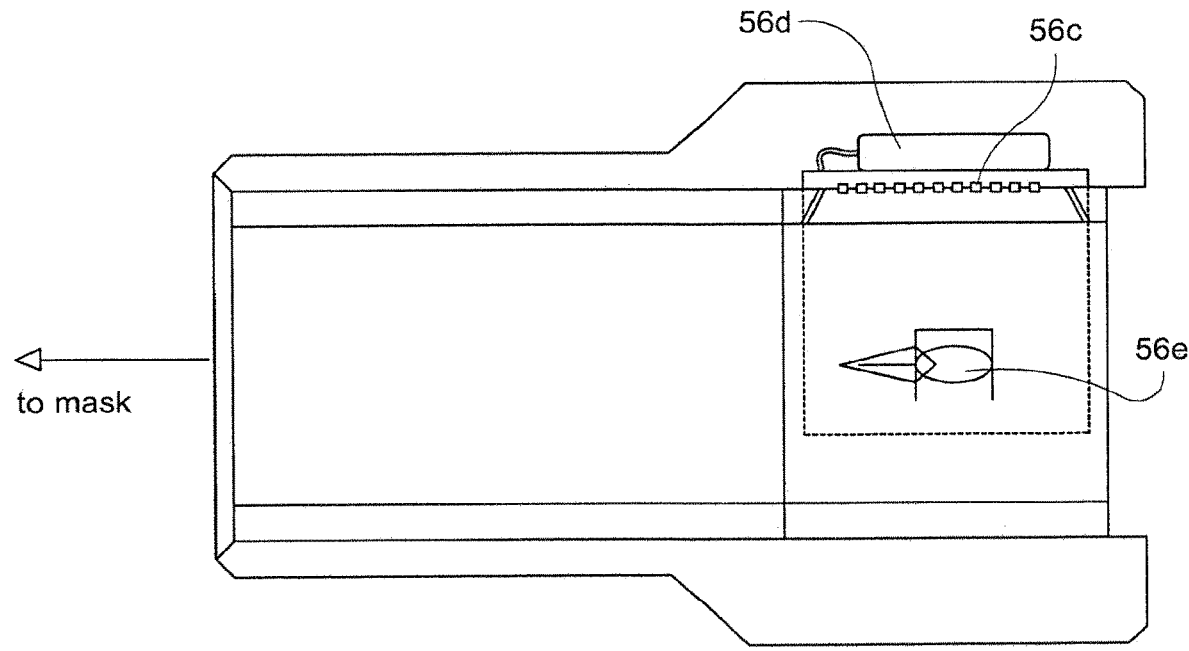
FIG. 34 schematically illustrates the circuit of the mask cuff provided on the connector block of the mask cuff.

Referring to FIGS. 33 and 34, the circuit on the flexible PCB 56*c* includes the thermal fuse or switch 56*d* and the thermal sensor 56*e*. One of the wires, e.g. 4*c*, may be used as a temperature sensing wire for sending a temperature signal to the power supply/controller 21. The other wires, e.g. 4*d*, 4*e*, may be used as heater wires to heat the tube 4*a* of the patient conduit 4. If the temperature exceeds a certain value, the thermal fuse 56*d* is configured to cut off current to the heater wires 4*d*, 4*e*.

The flexible PCB 56*c* and temperature sensor 56*e* and thermal fuse 56*d* should be provided on the connector block 56*a* as close to the inlet 5*a* of the patient interface 5 and the air path through the patient conduit 4 as possible. The mask connector or cuff 56 should also be formed as small as possible to permit its use with existing breathing apparatus. The use of the overmolded grip or cuff 56*b* is also useful for securing the patient conduit 4 to the connector block 56*a* and to secure the flexible PCB 56*c*, including the temperature sensor 56*e* and the thermal fuse 56*d* in place. The use of the overmolded material also helps to reduce or eliminate any locations where bacteria could grow.

The mask connector or cuff 56 as described herein is formed of biocompatible materials. The connector block 56*a* also includes an end 56*r* (FIG. 32) that includes a standard 22 mm female ISO taper for use with existing patient interfaces. The use of the overmolded material also eases manufacture and improves reliability of the mask connector or cuff.

Power Supply/Controller

Figure 35:
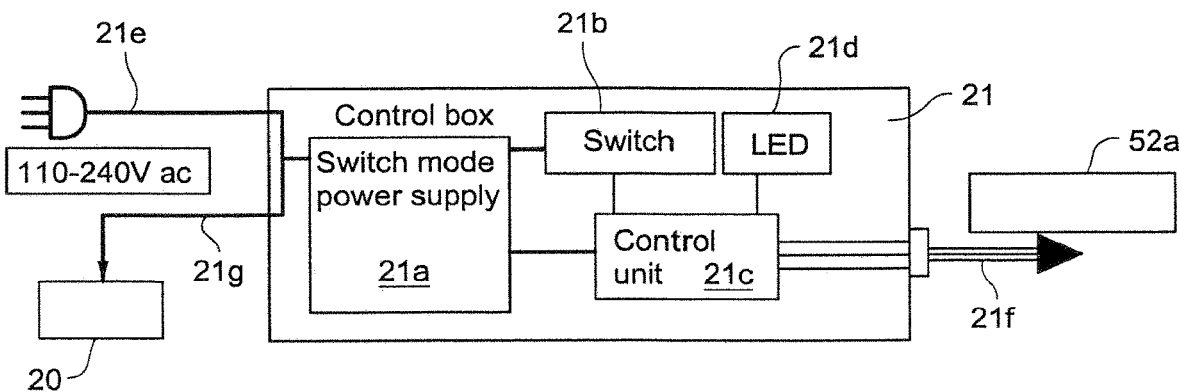
FIG. 35 schematically illustrates power supply/controller according to a sample embodiment of the present invention.

Referring to FIG. 35, the power supply/controller 21 comprises a switch mode power supply 21*a*, a switch 21*b*, a control unit 21*c*, and a plurality of LED's 21*d*. The power supply/controller 21 has an AC power input 21*e*, a DC power output 21*f*, and a bypass AC power lead 21*g* to the flow generator 20. The AC power input 21*e* may be, for example, 110-240V AC universal inputs. The switch 21*b* may be a MOSFET switch in series with the heater element controlled by the control unit 21*c*. The DC power output 21*f* may be, for example, a 500 mA regulated 5V DC, or a 1.3A, 24V DC output. At 24V the power output is 30 W.

The power input 21*e* is connected to the switch mode power supply 21*a* and the bypass 21*g* is connected to an AC power socket of the flow generator 20. The power supply/controller 21 is configured to provide power to the inlet conduit 10, regulate preset temperature levels at the patient interface 5, and act as an ON/OFF control.

The control unit 21*c* is a closed loop temperature control system. The temperature sensor 56*e* located in the mask cuff 56 provides the feedback signal through the wire 4*c* of the patient conduit 4 back to the control unit 21*c*. It should be appreciated, however, that the control may not rely on a feedback of a temperature signal. The control unit 21*c* may instead be configured to provide a predetermined amount of power to the output 21*f* without reliance, or dependence, on a temperature sensor signal.

The DC power output 21*f* supplies power to the inlet conduit 10 and the switch 21*b* is provided in series with the power output 21*f* and is controlled by the control unit 21*c*. The power regulation is based on an ON/OFF control technique. The power regulation has fixed duty cycles at a rate of about 95-99%. The OFF cycle, at a rate of about, for example 1-5%, is used for temperature sensing.

The LEDs 21*d* may include a green LED to indicate that power is on and being supplied to the inlet conduit 10. An amber LED may be provided to indicate that the power output 21*f* is ON, but not provided to the inlet conduit 10. A red LED may be provided to indicate a fault. Further LEDs may also be provided for indicating and/or controlling the temperature. Manually operable buttons (not shown) may be provided to the power supply/controller to allow control of the temperature by a patient or clinician in response to an indication of temperature by the LED's.

The control unit 21*c* is configured to produce a fixed power switching frequency and duty cycles for the power output 21*f* to heat the inlet conduit 10. The control unit 21*c* is also configured to sense the temperature via the signal sent by the temperature sensor 56*e* through wire 4*c*. Based on the sensed temperature, the control unit 21*c* is configured to regulate the temperature to a preset temperature when ambient temperature changes. The control unit 21*c* is further configured to record the preset temperature when the power control/supply 21 is turned off.

The control unit 21*c* may also latch a fault state when a fault is detected, and clear the fault by recycling power. If a fault occurs a fault detection circuit locks into a fault condition to send a fault signal to a driver block (FIG. 37*a*) the fault will continue until the power is turned OFF and ON again. The control unit 21*c* may be configured to detect faults, including any discontinuities in the wires 4*c*-4*e* and 10*c*-10*e*, any arcing and/or bad connections in the flow generator cuff 54 and/or the mask cuff 56. The control unit 21c may also detect low voltage.

The power output 21f is maintained in the OFF state by the control unit 21c when a fault is detected and is maintained in the OFF state until the power is recycled and the fault state is cleared.

The status of the power supply/controller 21 may be indicated through the LEDs 21d.

As shown, for example in FIGS. 5 and 8, the power supply/controller 21 may be separate from the flow generator 20 and the humidifier. There is no information exchange between the flow generator 20 and the humidifier and the closed loop control does not include control based on airflow rate, humidity level, and humidifier outlet temperature, for example. It should be appreciated, however, that information may be exchanged, for example through the sensing wire 4c. The control described above prevents "rain out" in the patient conduit 4 and delivers the humidified air to the patient interface 5.

It should be appreciated that the power supply/controller 21 may be integrated with the flow generator 20 or the humidifier control system. Information may be provided to the integrated power supply/controller regarding the operation of the flow generator, the humidifier, and ambient air. By integrating the power supply/controller with the flow generator 20 or the humidifier, the system will be more able to control the temperature at the patient interface 5, the humidity levels and "rain out" at a wider range of ambient temperature and humidities.

Figure 36:
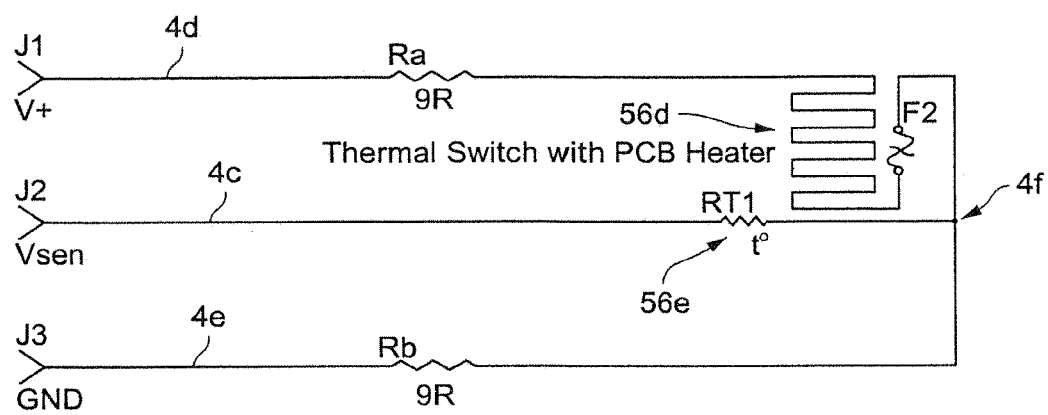
FIG. 36 schematically illustrates a three wire heated tube according to a sample embodiment of the invention.

Referring to FIG. 36, a three wire heated tube or conduit according to a sample embodiment of the invention is illustrated. The wires 4d, 4e may be formed, for example, from a 25 m long wire having a diameter of 0.23 mm, and be formed, for example, of copper. The sensing wire 4c may be connected to the heating wires 4d, 4e at a connection point 4f that is approximately the middle of the wire forming the wires 4d, 4e and divides the wire into two resistances Ra, Rb. The total resistance Ra+Rb may be equal to about 15-21Ω, for example about 18Ω, at 20°-26° C., for example about 23° C. The total resistance Ra+Rb is about 18Ω, and about 21Ω, when the wire resistors are heated up to about 33° C. using a 24V DC supply at a power of about 30 W. As discussed above, the DC voltage V+ may be supplied across J1 and J3 at a duty cycle of, for example, about 95-99%. The resistances Ra, Rb generate heat during the flow of current through the wires 4d, 4e to heat the conduit 4. The sensing voltage Vsen may be determined during the 1-5% OFF cycle. During the OFF cycle, the switch 21b is activated by the control unit 21c to switch the system into a sensing state and sensing current from J1 passes resistance Ra and resistance RT1 of the temperatures sensor 56e back to J2. The resistance RT1 of temperature sensor 56e may be about 1-50 kΩ and resistance Rb may be about half of Ra+Rb, or about 5-15Ω, for example about 10Ω, so Rb is omitted.

Although the sensing wire 4c is disclosed as being connected to the temperature sensor 56e, it should be appreciated that the sensing wire may be connected to a different sensor, such as a pressure sensor, for example in the event that the control is not a feedback control based on the detected temperature.

The fuse F2 of the thermal circuit 56d is thermally coupled to the heater track of the PCB 56c. The PCB 56c may be, for example, about 0.05-0.15 mm thick, for example about 0.1 mm thick, have a resistance of about 0.05-0.15Ω, for example about 0.1Ω, and a power output of about 0.12-0.24 W, for example about 0.18 W. As discussed above, one side of the PCB 56c faces the open window 56j so the PCB 56c contacts the air in the patient conduit 4. The air flowing in the conduit therefore cools the PCB 56c to just above the temperature of the air in the conduit. If the flow generator stops, or the air flow through the conduit is blocked, the temperature of the PCB 56c will rise and trip the fuse F2 to protect the patient conduit 4 from damage. The temperature sensor 56e and the fuse F2 of the thermal circuit 56d thus provide over air temperature protection, tube over heating protection, and low airflow protection. The thermal circuit 56d may include a thermostat, for example a bi-metal strip, instead of the fuse, and an increase in impedance of the thermostat would act to suppress, or stop, an increase in the current.

As the patient conduit 4 delivers the humidified air to the patient interface 5, the power supply/controller 21, the mask cuff 56 and its components, and the patient conduit 4 should comply with safety standards for temperature regulation, for example, ISO 8185. Under normal operating conditions, the patient or clinician should be able to set the temperature of the air delivered to the patient interface 5 from ambient to about 30° C. If no alarm system or indicator is provided to the system, in accordance with ISO 8185, sections 51.61-51.8, under normal and single fault conditions, the temperature of the air delivered to the patient interface 5 should not exceed about 40°-42° C., for example about 41° C. This maximum temperature (e.g. 41° C.) is under the maximum energy level of 43° C. at 100% RH. The fuse F2 of the thermal circuit 56d may be chosen to trip off at the maximum temperature.

Referring again to FIG. 36, the three wire (4c-4e) electrical circuit of the patient conduit 4 includes the heating elements Ra, Rb in series with the heater track and fuse F2 of the PCB 56c, the wire 4c for supplying the sensing voltage Vsen, and the thermal sensor 56e including the thermal resistor TR1 attached to the middle 4f of the of the heater wires 4d, 4e. The electrical circuit has two states: ON and OFF. In the ON state, also referred to as the heating state, the wire 4d is connected at J1 to the voltage V+, for example the 24V DC from the power output 21f. The heating current flows through J3, wires 4d, 4e, J4 and the switch 21b and into ground GND. In the ON state, the sensing voltage Vsen at J2 will not sense the air temperature, but will sense about half of voltage V+, e.g. about 12V.

In the OFF state, the switch 21b is switched off and the heater wires 4d, 4e will be pulled up by V+, e.g. about 24V, and the sensing current passes through J1, Ra, RT1 and back to J2.

The power supply/controller 21 may include circuits for performing numerous functions. These circuits may include: 1) a power switching control circuit; 2) a tube interface and gate drive circuit (driver block); 3) a fault detection and latching circuit (fault detection latch); 4) a temperature preset/control circuit; and 5) a start up and indication circuit.

Power Supply/Controller Circuits

A sample embodiment of the circuits of the power supply/controller 21 is shown in FIG. 37a. The circuit includes a temperature control circuit configured to control the temperature of the heated conduit(s), a fault detection latch, a sensing circuit and a driver block. The driver block is connected to the switch 21b, which may be a MOSFET.

Referring to FIGS. 37b-1-37b-4, a sample embodiment of the circuit of FIG. 37a may be based on, for example, an UC2843 control IC, available from Texas Instruments. It should be appreciated that other control circuits may be used. The power switching control circuit has chip over-current and over-voltage protections which can be used for error handling. The power switching control circuit may also have an RC clock and under-voltage lockup and a push-pull output driver. By setting the oscillating RC clock such that R12=22,000Ω and C5=330 nF, the switch frequency may be set at 138 Hz. The time period for such a frequency is determined by T=R12×C15 (22,000×0.00000033)=7.26 mS. By ratio of R12 and C5, the power switching control circuit provides a 100 ρS OFF period, and the duty cycle is thus 100 ρS/7.26 mS=1.38%.

At normal heating conditions, the power switching control circuit of FIGS. 37b-1-37b-4 drives the transistor gate of the switch 21b at about 98.62% duty cycles. The ON state of the circuit cannot be interrupted by Vfb signals. At the Vfb critical point, the gate signal can be shown as 50% 69 Hz outputs.

The power switching control circuit has enable input through the Vfb pin. When any of the signals through D3 and D4 to low, it will disable the output of the switch 21c. The sensing current Isen is not used for this application as R10 and R20 set the sensing voltage Vsen below 1V.

Referring again to FIGS. 37a and 37b-1-37b-4, the sensing voltage Vsen has two functions: 1) when the heater power is ON, the sensing voltage Vsen detects the heater wires continuity, or any arcing or bad connections by sensing middle voltage V+; and 2) when the heater power is OFF, the sensing voltage Vsen senses the air temperature via the RT1 and R13 divider voltages. The Q2, Q3 network provides right logic for sensing operations and MOSFET Q3 provides low impedance (Rdson) for temperature sensing. Q4 MOSFET gate drives network R23, R25 limiting the maximum gate voltage; R24 and D5 together with R23 control the Q4 switch off speed.

The fault detection circuit operates when heater power is ON. The Vsen signal is fed into a window comparator, for example an ultra-power quad comparator, such as the LP339AM, available from National Semiconductor. U6B, U6D; R31, R36 and R43 divider provide a +/−2V window voltage at 12 Volt; the output of window comparator signals will feed into second stage of the comparator U6C.

The second stage of comparator samples the Q4 gate signal as a base line and detecting the error signal from window comparator output. When system has no fault detected, window comparator outputs as high impedance, R34 and R40 divider has higher voltage out then inverting comparator input R33 and R42 divider network, U6C will output high.

When the system has a fault detected, window comparator outputs low, R34 and R40//R35 divider has lower voltage then inverting comparator input R33 and R42 divider network, U6C will output low to U2A latch CLR pin.

When latch CLR pin 1 receives a low signal the Q pin 5 will output a latched fault signal, it will kill the U3 output switching signals. The latch may be, for example, a 74HCT74D U2A from Fairchild Semiconductor.

The temperature sensing operation is only performed during the power OFF period. The air temperature sensor RT1 and divider base resistor R13 provides the temperature information Vsen, it directly feed into the comparator U6A inverting input, a potentiometer and it's network does the temperature preset function. The output of this comparator drives D4 and controls the U3 switch output.

The start up circuit provides a 140 mS delay when system start up and it will reset the latch. After reset, the system will at ON state. The start up circuit may be, for example, an IC U4 TCM809, available from TelCom Semiconductor, Inc.

The accuracy of temperature measurement is based on two parts: 1) sensing accuracy; and 2) accuracy of reference. Sensing accuracy depends on NTC thermistor RT1 and series resistor R13. For example, a good NTC sensor RT1 may have up to a 1-5%, for example about 3%, accuracy tolerance; the series resistor R13 may have up to a 0.5-1.5% tolerance, for example about a 1% tolerance. The accuracy of the temperature preset circuit is determined when the port is at highest setting (30° C.). The port resistor is 0Ω and the accuracy is dependent on the 1% resistor network. However, when the port is set to the lowest setting, 20% of the port resistor tolerance will be added in.

The conduits 4 and 10 will overheat when there is no gas flow in the tubes. The heat can be accumulated in the tube, if the tube is covered, for example under a quilt, and the heater element temperature can rise to 120-150° C. The heat can accrue when the thermal switch is exposed in cold air, but part of the tube was covered, for example under the quilt. For this reason, a no flow or low flow signal from the flow generator should able to trip off the heated tube power supply.

A three way connector is provided between thermistor sensor RT1 and the control unit 21c. Any bad connection on the contactor will cause increasing impedance on the sensing circuit; for NTC thermistor RT1 it will lower the temperature readings, and it can cause air temperature rise and may trip the thermal switch 21b at the tube.

There are two ways to solve fault states in the temperature sensing. A first way is to change the voltage divider logics, as contact resistance is high the air temperature goes low. The other way to protect the sensing contactor is to off-set the sensing wire by changing R6 and R31 to 8.2 kΩ. This offset reference voltage can detect the high impedance connectors.

Cuff Configurations

Figure 38:
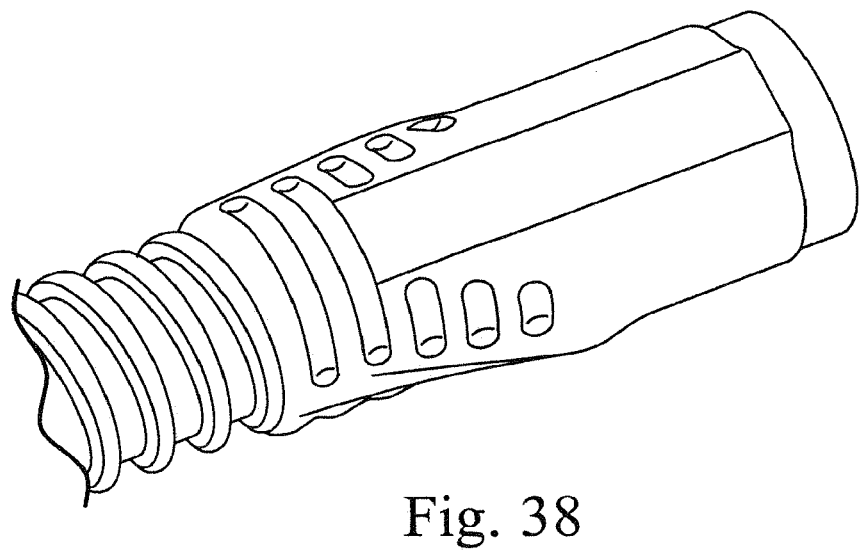
FIGS. 38-40 are perspective views of overmolded grip portions for the flow generator cuff and/or mask cuff.
Figure 39:
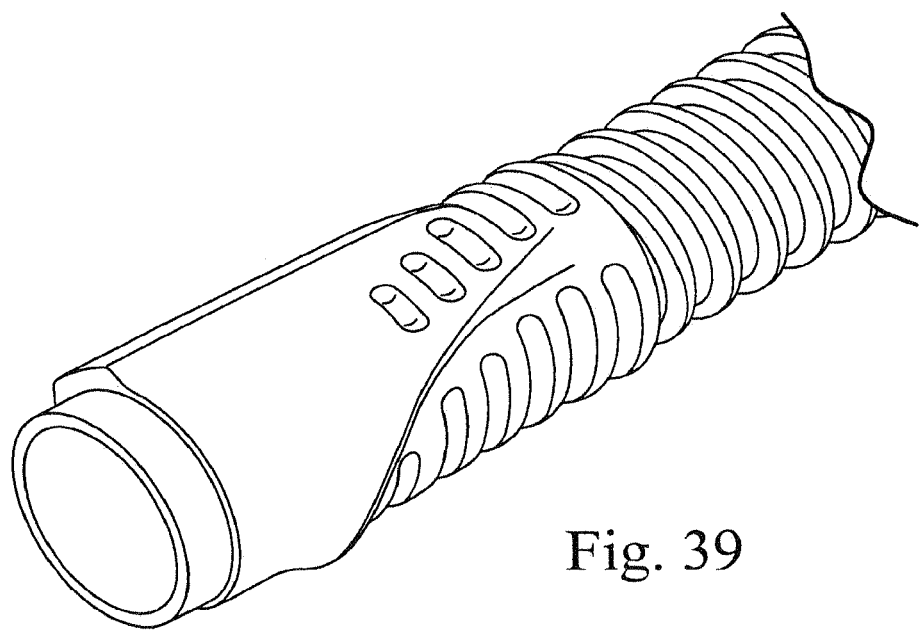
Figure 40:
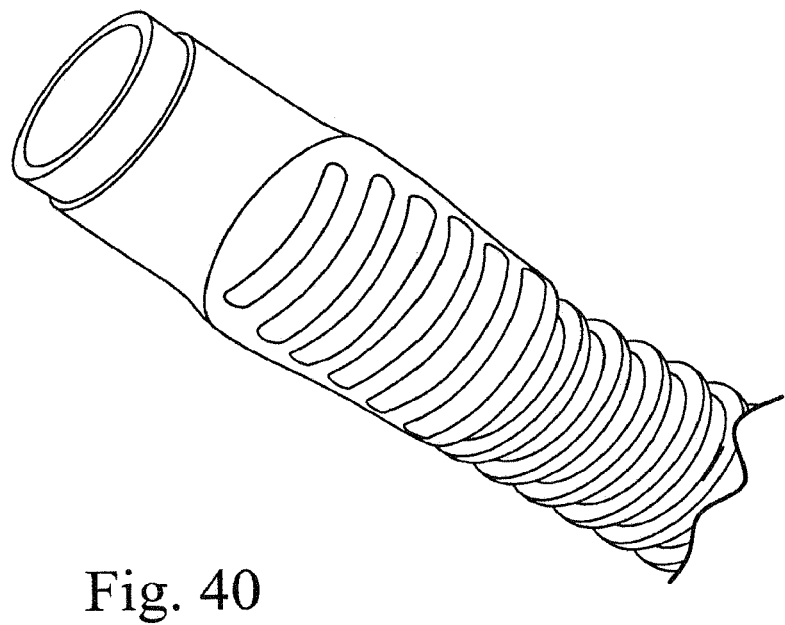

As shown in FIGS. 38-40, the configuration of the inlet conduit connector cuff and/or the patient conduit and mask connector cuff may take various forms. Each of the mask connector or cuff configurations shown and described herein may include grip features, and sufficient strain relief features to improve the flexibility of the connector or cuff.

Tube Configurations

Figure 41:
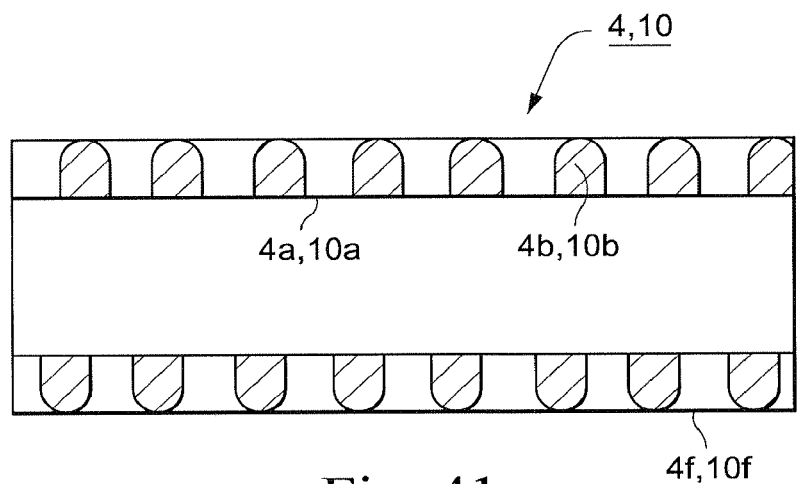
FIG. 41 illustrates a conduit according to a sample embodiment of the invention.

Referring to FIG. 41, the inlet conduit 10 and/or the patient conduit 4 may include an inner tube 4a, 10a, a helical rib 4b, 10b, and an outer tube 4f, 10f. The outer tube 4f, 10f may be formed of the same material as the inner tube 4a, 10a. The outer tube 4f, 10f may also be provided with a fleece or flocked material to improve the feel and/or grip of the conduit, and/or to improve the thermal insulation properties of the tube and/or the visual appeal. If the outer tube 4f, 10f is not provided, the outer surfaces of the inner tube 4a, 10a and the helical rib 4b, 10b may be provided with a fleece or flocked material for similar reasons.

Figure 42:
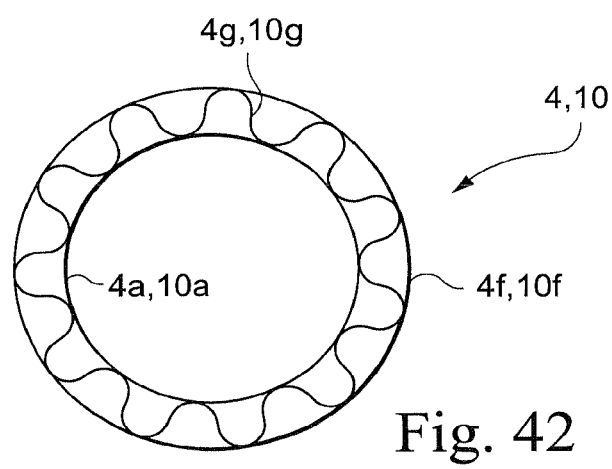
FIG. 42 illustrates a conduit according to a sample embodiment of the invention.

Referring to FIG. 42, the inlet conduit 10 and/or the patient conduit 4 may include an inner tube 4a, 10a and an outer tube 4f, 10f spaced by corrugations 4g, 10g. The corrugations 4g, 10g may extend axially along the conduit 4, 10, or may extend helically along the conduit 4, 10. Wires may be provided within the corrugations 4g, 10g, between the inner tube 4a, 10a and the outer tube 4f, 10f. The corrugations may also be used to provide a supplemental gas flow along the conduit 4, 10, or to provide a flow of liquid, for example water, to regulate the temperature of the gas flow in the conduit 4, 10. The corrugations may also be used to exhaust gas, for example from the patient's exhalation, from the patient interface. The outer tube 4f, 10f may also be covered in fleece or flocked material.

Patient Conduit, Mask Connector Cuff, and Flexible Circuit

Figure 43:
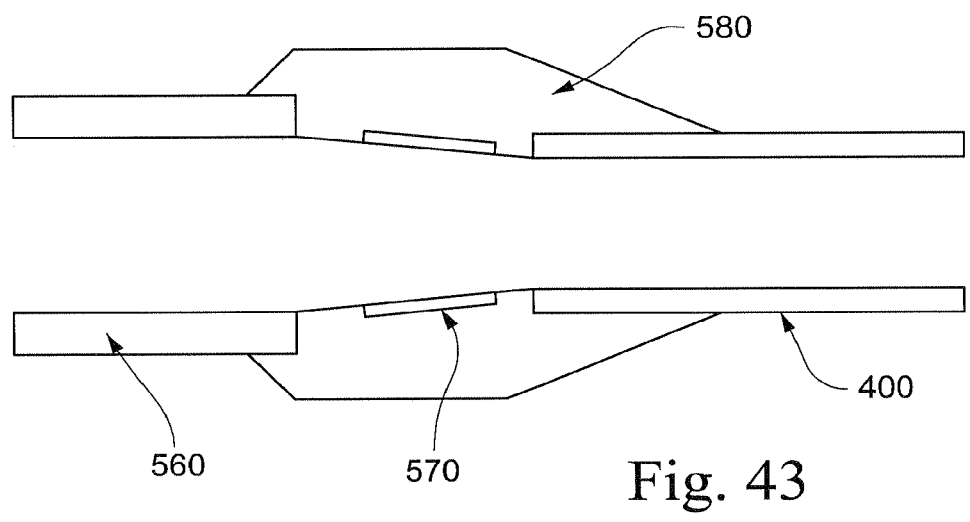
FIG. 43 illustrates a patient conduit and mask cuff according to a sample embodiment of the invention.

Referring to FIG. 43, a patient conduit 400, mask connector cuff 560 and flexible circuit 570 according to another sample embodiment are illustrated. The patient conduit 400 is connected to the mask cuff 560 by an overmold material 580 that encompasses the flexible circuit 570. The overmold material 580 is overmolded onto the patient conduit 400 and the mask cuff 560. The flexible circuit 570 may include the tube wires, sensors, fuses and other components described above in relation to the other sample embodiments.

The mask cuff 560 may be formed as a separate part that is connected to the patient conduit 400 through the overmold material 580. Alternatively, the mask cuff 560 may be formed as a single piece with the overmold material. 580.

Although the invention has been herein shown and described in what is conceived to be the most practical and preferred embodiments, it is recognized that departures can be made within the scope of the invention, which is not to be limited to the details described herein but is to embrace any and all equivalent assemblies, devices and apparatus. For example, the heating wires may be PTC elements with a voltage regulation to limit the temperature of the wires ad/or the air in the conduit(s). As another example, one or more PTC or NTC wires may be used in conjuction with a resistor to limit the temperature of the wires and the air. As a further example, NTC wires may be used with a current regulator, or a measure resistance, to limit the temperature of the heating wires. The temperature sensing and heating may also be performed using only two wires.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the invention relates.

What is claimed is:

1. A heated conduit configured to be connected to and receive pressurized breathable gas from a respiratory unit, the heated conduit comprising:
   a first cuff configured to be attached to the respiratory unit, the first cuff comprising a tubular air inlet portion that is configured to receive the pressurized breathable gas and an electrical connector portion that is adjacent to the tubular air inlet portion and comprises three electrical terminals, the three electrical terminals being configured to engage an electrical connector of the respiratory unit;
   a second cuff comprising a tubular air outlet configured to pass the pressurized breathable gas towards an inlet of a patient interface;
   a flexible tube portion with a first end connected to the first cuff and a second end connected to the second cuff, the flexible tube portion comprising a central lumen and a helical rib wrapped around the central lumen, the central lumen forming a continuous gas flow path with the tubular air inlet portion of the first cuff and the tubular air outlet of the second cuff;
   a sensing device positioned within the second cuff, the sensing device being configured to output a signal indicative of a condition inside the heated conduit; and
   a grouping of wires supported within the helical rib of the flexible tube portion, the grouping of wires comprising a pair of heating wires configured to generate heat and a signal wire configured to carry the signal that is output by the sensing device, each of the heating wires and the signal wire being connected to a corresponding one of the three electrical terminals of the electrical connector portion of the first cuff,
   wherein the pair of heating wires and the signal wire are positioned in a side-by-side arrangement within the helical rib so that the pair of heating wires and the signal wire form a row in which one of the pair of heating wires and the signal wire is between the other two of the pair of heating wires and the signal wire,
   wherein the three electrical terminals are positioned in a side-by-side arrangement that forms a row in which one of the electrical terminals is between the other two electrical terminals, and
   wherein the first cuff and the second cuff have different shapes.

2. The heated conduit of claim 1, wherein the first cuff comprises a rim configured to act as a stop and abut an end of an air outlet of the respiratory unit.

3. The heated conduit of claim 1, wherein the second cuff comprises an internal ridge configured to act as a stop and abut an end of the inlet of the patient interface.

4. The heated conduit of claim 1, wherein the first cuff comprises finger grips.

5. The heated conduit of claim 1, wherein the first cuff and the second cuff are overmolded onto opposing ends of the flexible tube portion.

6. The heated conduit of claim 1, wherein the sensing device comprises a temperature sensor, and the signal wire is configured to convey a temperature signal.

7. The heated conduit of claim 6, wherein the temperature sensor is a thermistor.

8. The heated conduit of claim 7, wherein the pair of heating wires are connected to one end of the thermistor and the signal wire is connected to another end of the thermistor.

9. The heated conduit of claim 1, wherein the pair of heating wires and the signal wire extend to the second cuff.

10. A respiratory apparatus configured to generate and deliver pressurized breathable gas to a patient's airways, the respiratory apparatus comprising:
    a respiratory unit configured to pressurize the breathable gas;
    the heated conduit of claim 1, the first cuff of the heated conduit being configured to connect to an air outlet of the respiratory unit; and
    a printed circuit board (PCB) with a control circuit configured to control the heated conduit.

11. The respiratory apparatus of claim 10, wherein the respiratory unit is a flow generator or a combined flow generator and humidifier.

12. The respiratory apparatus of claim 10, further comprising a thermal fuse configured to terminate a current supplied to the pair of heating wires when a temperature in the flexible tube portion exceeds a threshold temperature.

13. The respiratory apparatus of claim 10, further comprising the patient interface with the inlet, wherein the inlet is an air inlet configured to receive the pressurized flow of breathable gas from the heated conduit, the patient interface being configured to sealingly engage a patient's face.

14. The respiratory apparatus of claim 13, wherein the air inlet of the patient interface is an elbow.

15. A heated conduit configured to be connected to and receive pressurized breathable gas from a respiratory unit, the heated conduit comprising:
- a first connector with a tubular air inlet and an electrical connector located outside a perimeter of the tubular air inlet, the tubular air inlet being configured to engage an air outlet of the respiratory unit, the electrical connector comprising a set of three electrical contacts configured to engage an electrical connector of the respiratory unit;
- a second connector with a tubular air outlet configured to pass the pressurized breathable gas toward an inlet of a patient interface;
- a flexible tube portion with a first end attached to the first connector and a second end attached to the second connector, the flexible tube portion comprising a central lumen configured to convey the pressurized breathable gas from the tubular air inlet of the first connector to the tubular air outlet of the second connector; and
- a rib helically wrapped around the length of the flexible tube portion, the rib containing a pair of heating wires and a signal wire, which extend at least the length of the flexible tube portion, the heating wires being configured to heat the pressurized breathable gas flowing through the central lumen of the flexible tube portion, the signal wire being configured to convey a signal indicative of a condition within the central lumen,
- wherein each of the heating wires and the signal wire is connected to a corresponding one of the three electrical contacts of the electrical connector,
- wherein the pair of heating wires and the signal wire are positioned in a side-by-side arrangement within the rib so that the heating wires and the signal wire form a row in which one of the wires is between the other two wires,
- wherein the three electrical contacts are positioned in a side-by-side arrangement that forms a row in which one of the electrical contacts is between the other two electrical contacts, and
- wherein the first connector and the second connector have different shapes.

16. The heated conduit of claim 15, wherein the first connector comprises a rim configured to act as a stop and abut an end of an air outlet of the respiratory unit, and the second connector comprises an internal ridge configured to act as a stop and abut an end of the inlet of the patient interface.

17. A respiratory apparatus configured to deliver pressurized breathable gas to a patient's airways, the respiratory apparatus comprising:
- a respiratory unit configured to pressurize the breathable gas;
- the heated conduit of claim 16, and
- a printed circuit board (PCB) with a control circuit configured to control the heated conduit.

18. The respiratory apparatus of claim 17, wherein the respiratory unit is a flow generator or a combined flow generator and humidifier.

19. The respiratory apparatus of claim 17, further comprising a thermal fuse configured to terminate a current supplied to the pair of heating wires when a temperature in the flexible tube portion exceeds a threshold temperature.

20. The respiratory apparatus of claim 17, further comprising the patient interface with the inlet, wherein the inlet is an air inlet configured to receive the pressurized flow of breathable gas from the heated conduit, the patient interface being configured to sealingly engage a patient's face.

21. The respiratory apparatus of claim 20, wherein the air inlet of the patient interface is an elbow.

22. The heated conduit of claim 15, wherein the first connector comprises finger grips.

23. The heated conduit of claim 15, wherein the first connector and the second connector are overmolded onto opposing ends of the flexible tube portion.

24. The heated conduit of claim 15, further comprising a sensing device located within the second connector, the sensing device being configured to output a signal indicative of a condition inside the heated conduit.

25. The heated conduit of claim 24, wherein the sensing device comprises a temperature sensor, and the signal wire is configured to convey a temperature signal.

26. The heated conduit of claim 25, wherein the temperature sensor is a thermistor.

27. The heated conduit of claim 26, wherein the pair of heating wires are connected to one end of the thermistor and the signal wire is connected to another end of the thermistor.

* * * * *